United States Patent
Brugger et al.

(10) Patent No.: US 10,344,874 B2
(45) Date of Patent: *Jul. 9, 2019

(54) CLAMP DEVICE AND METHODS FOR MAKING AND USING

(71) Applicant: NXSTAGE MEDICAL, INC., Lawrence, MA (US)

(72) Inventors: James M. Brugger, Newburyport, MA (US); William J. Schnell, Libertyville, IL (US)

(73) Assignee: B. BRAUN MEDICAL INC., Bethlehem, PA (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/664,728

(22) Filed: Jul. 31, 2017

(65) Prior Publication Data
US 2017/0328482 A1 Nov. 16, 2017

Related U.S. Application Data

(63) Continuation of application No. 14/348,509, filed as application No. PCT/US2013/042695 on May 24, 2013, now Pat. No. 9,829,113.
(Continued)

(51) Int. Cl.
*F16K 7/06* (2006.01)
*B29C 37/00* (2006.01)
*A61M 39/28* (2006.01)

(52) U.S. Cl.
CPC ............. *F16K 7/06* (2013.01); *A61M 39/284* (2013.01); *B29C 37/0003* (2013.01); *Y10T 24/44906* (2015.01)

(58) Field of Classification Search
CPC . F16K 7/06; F16K 7/065; F16K 7/066; F16K 7/063; B29C 37/0003; A61M 39/28; A61M 39/284; Y10T 24/44906
(Continued)

(56) References Cited

U.S. PATENT DOCUMENTS 3,822,052 A  7/1974 Lange
4,053,135 A  10/1977 Saliaris
(Continued)

FOREIGN PATENT DOCUMENTS

EP   0637456 A1  2/1995
EP   0995461 B1  9/2004
(Continued)

OTHER PUBLICATIONS

"Qosina Offers New Slotted Pinch Clamps," Qmed Supplier News [online], [retrieved on May 15, 2015]. Retrieved from the Internet: URL: http://www.qmed.com/news/supplier/qosina-offers-new-slotted-pinch-clamps.
(Continued)

*Primary Examiner* — Craig J Price
*Assistant Examiner* — Andrew J Rost
(74) *Attorney, Agent, or Firm* — Potomac Law Group, PLLC; Mark Catan

(57) ABSTRACT

Releasable tubing pinch clamps of a generally U-shaped configuration are described. The embodiments include ones that prevent cross-clamping of the tube by various interlocking features on riser portions of the clamp. Methods and molds for making the pinch clamps are also described. For example, a pinch clamp can have a strip that curves so that its ends can be brought together by manually squeezing the strip at its end, which oppose each other as a result of the strip curve. The strip ends have locking edges or surfaces that cause the strip ends to interferingly engage with each other and lock together. The strip also has opposing pinch projections that can pinch a tube.

20 Claims, 12 Drawing Sheets

Related U.S. Application Data

(60) Provisional application No. 61/651,842, filed on May 25, 2012, provisional application No. 61/762,214, filed on Feb. 7, 2013.

(58) Field of Classification Search
USPC .................................................. 251/10, 4, 9
See application file for complete search history.

(56) References Cited

U.S. PATENT DOCUMENTS

| | | | |
|---|---|---|---|
| 4,453,295 | A | 6/1984 | Laszczower |
| 4,589,626 | A | 5/1986 | Kurtz et al. |
| 4,802,650 | A | 2/1989 | Stricker |
| 5,035,399 | A | 7/1991 | Rantanen-Lee |
| 6,089,527 | A | 7/2000 | Utterberg |
| 6,113,062 | A | 9/2000 | Schnell et al. |
| D431,650 | S | 10/2000 | Guala et al. |
| 6,142,979 | A | 11/2000 | McNally et al. |
| 6,161,812 | A | 12/2000 | Guala et al. |
| 6,196,519 | B1 | 3/2001 | Utterberg |
| 6,234,448 | B1 | 5/2001 | Porat |
| 6,592,558 | B2 | 7/2003 | Quah |
| 7,234,677 | B2 | 6/2007 | Zerfas |
| 8,474,784 | B2 | 7/2013 | Kashmirian et al. |
| 8,485,495 | B2 | 7/2013 | Zerfas |
| 8,801,677 | B2 | 8/2014 | Wallin |
| 9,060,920 | B2 | 6/2015 | Hirabuki |
| 9,162,044 | B2 | 10/2015 | Traversaz |
| 9,498,616 | B2 | 11/2016 | Mathias et al. |
| 9,592,376 | B2 | 3/2017 | Haecker et al. |
| 2010/0096570 | A1 | 4/2010 | Kashmirian et al. |
| 2010/0152681 | A1 | 6/2010 | Mathias |
| 2010/0249510 | A1 | 9/2010 | Yamada |
| 2010/0268161 | A1 | 10/2010 | Traversaz |
| 2011/0112489 | A1 | 5/2011 | Balteau |
| 2011/0163533 | A1 | 7/2011 | Snyder et al. |
| 2012/0035553 | A1 | 2/2012 | Lombardo et al. |
| 2012/0232497 | A1 | 9/2012 | Singh |
| 2013/0110087 | A1 | 5/2013 | Kane |

FOREIGN PATENT DOCUMENTS

| | | |
|---|---|---|
| EP | 2332611 A1 | 6/2011 |
| EP | 2512548 A1 | 10/2012 |

OTHER PUBLICATIONS

"SidePinch® Clamps," Hotfrog [online], Aug. 2009 [retrieved on May 15, 2015]. Retrieved from the Internet: URL: http://www.hotfrog.com/Companies/SidePinch-R-Clamp/SidePinch-R-Clamps-26629.

International Search Report and Written Opinion for International Application No. PCT/US2013/042695 dated Oct. 17, 2013.

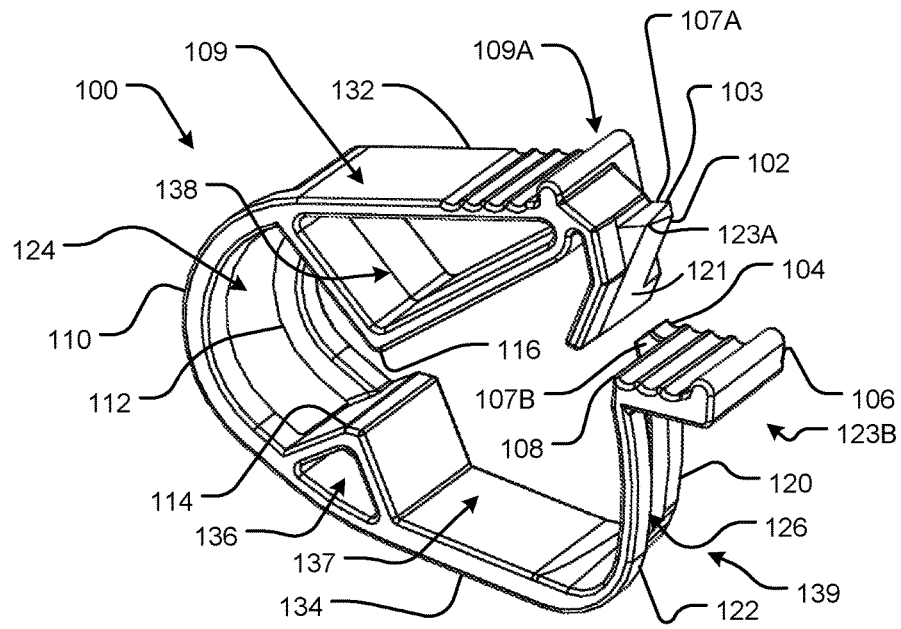
Fig. 2A
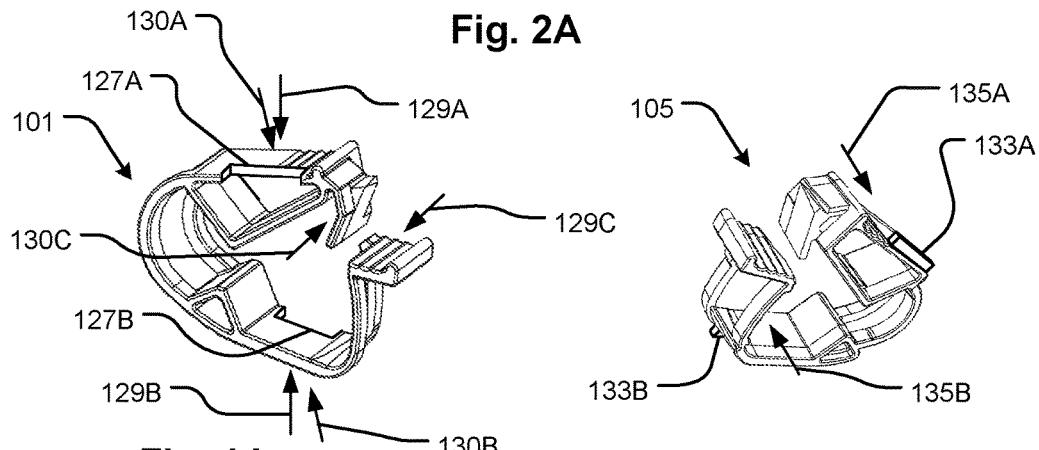
Fig. 1A
Fig. 1B
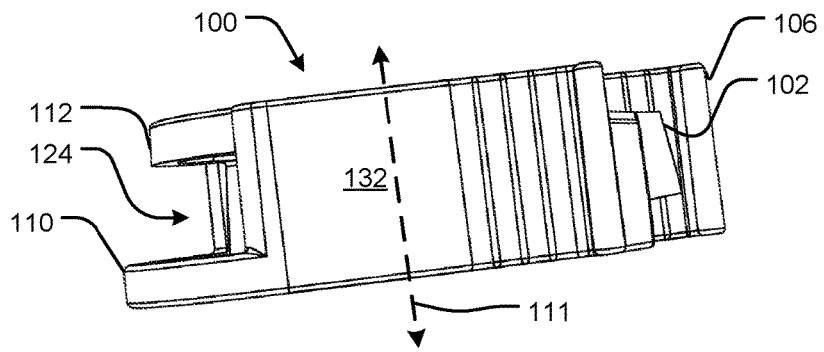
Fig. 2B

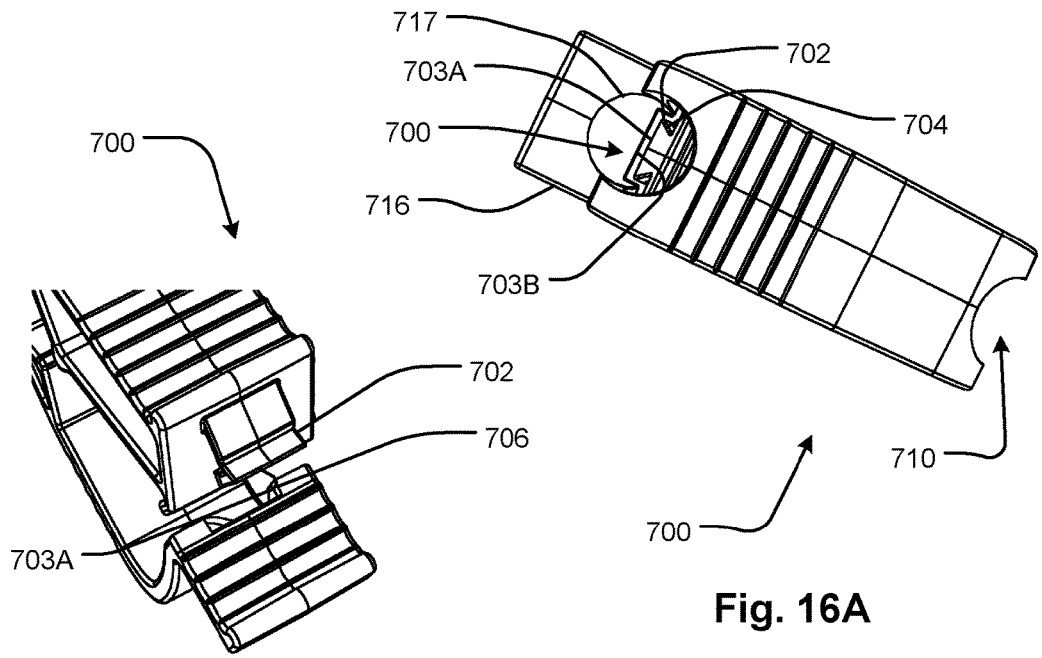
Fig. 16A
Fig. 16B
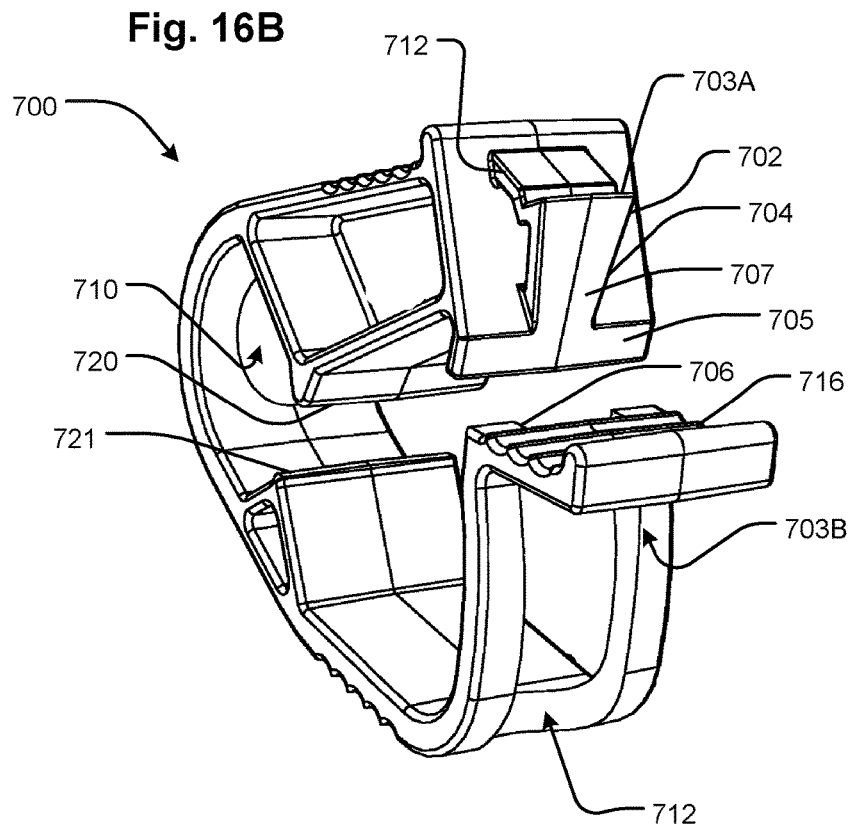
Fig. 16C

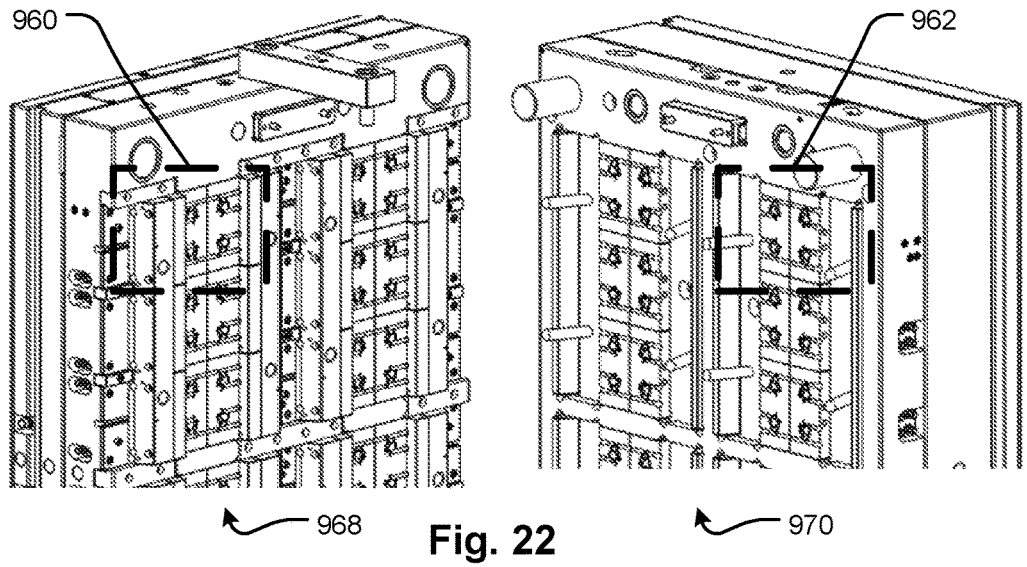
Fig. 22
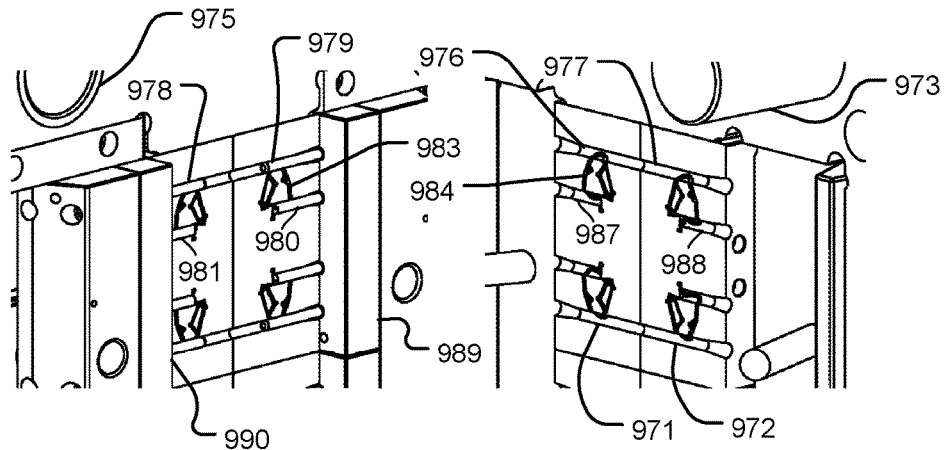
Fig. 23A   Fig. 23B
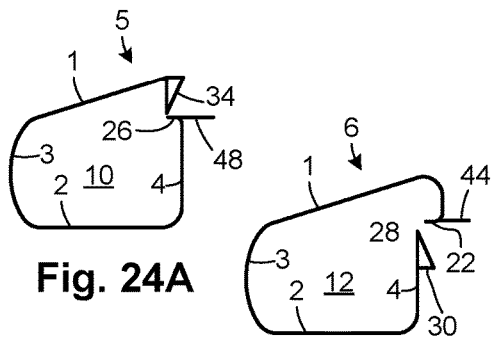 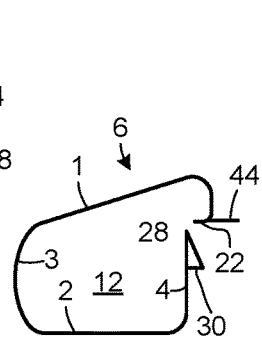
Fig. 24A   Fig. 24B
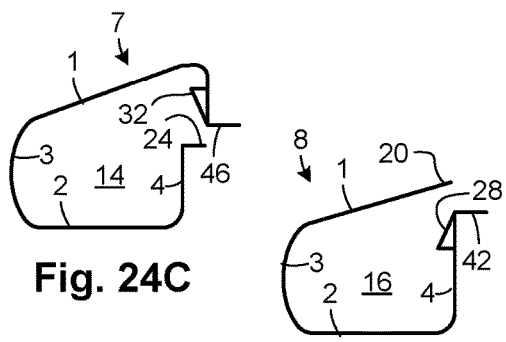 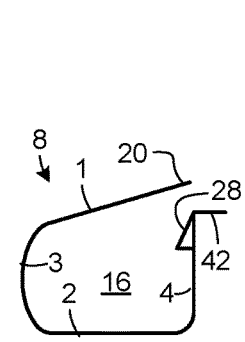
Fig. 24C   Fig. 24D

CLAMP DEVICE AND METHODS FOR MAKING AND USING

CROSS-REFERENCE TO RELATED APPLICATIONS

This application is a continuation of U.S. patent application Ser. No. 14/348,509 filed Mar. 28, 2014, which is a U.S. national stage filing under 35 U.S.C. § 371 of International Application No. PCT/US2013/042695 filed May 24, 2013, which claims the benefit of U.S. Provisional Application No. 61/651,842 filed May 25, 2012 and U.S. Provisional Application No. 61/762,214 filed Feb. 7, 2013, each of which is incorporated herein by reference in its entirety.

BACKGROUND

One-piece plastic clamps used to pinch off plastic tubing, such as polyvinyl chloride (PVC) tubing are well known. Examples are found in U.S. Pat. Nos. 6,196,519, 6,089,527, D431650, and 6161812. Known clamps are formed from a single strip of plastic in which the respective ends are curved towards each other to engage together in a snap-fit. The curved portion may generate a restoring force that is opposed by interfering relationship of catches at the ends of the strip, thereby providing the snap-fit engagement. Pinch projections on the inner side of the strip squeeze the tubing shut when the ends of the strip are engaged. The tubing can be opened by releasing and permitting the separation of the engaged ends.

The strip portion of known clamps may have two opening in the middle of the strip. These openings may be arranged so that the tube can pass between the openings and through the middle of the strip so that it is positioned between the pinch projections.

The engagement of known clamps can be performed improperly such that cross-clamping occurs. In this situation, it is possible for the pinch clamp to spontaneously disengage or to pinch the tube incompletely or with inadequate force. Also, clamps are used in large number in disposable tubing sets and it is desirable for them to have high performance but low cost. For example, pinch clamps have been used in the dialysis blood tubing sets for many years. Thus, there is a continuing need for improvements in the design of clamps to provide reliability, ease of use, and low cost.

SUMMARY

Various pinch clamp embodiments have structures that allow the pinch clamps to be molded without slides or complex injection mold actions permitting a larger number of clamps to be made in a smaller simpler mold assembly. The designs also provide integrated features that prevent cross-clamping without relying on material to provide shape integrity, rigidity or strength. As a result, the pinch clamps can be made from a lower mass of material and the cost reduced further.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 1A and 1B show respective features that can be provided in a pinch clamp to urge an anti-cross-clamping surfaces against each other to maintain ends of the pinch clamp strip in alignment for proper clamping.

FIG. 2A shows a pinch clamp according to a first embodiment of the disclosed subject matter from a first perspective.

FIG. 2B shows the pinch clamp according to the embodiment of FIG. 2A from a second perspective showing a top surface that is typically intended to be pushed by the thumb of the user.

FIGS. 16A, 16B, and 16C illustrate symmetric embodiments with an anti-cross-clamping feature according to embodiments of the disclosed subject matter.

FIGS. 22, 23A and 23B illustrate embodiments for making a pinch clamp generally of the type described in the embodiments of FIGS. 16A, 16B, 16C, and 18A.

FIGS. 24A, 24B, 24C, and 24D illustrate schematic diagrams of alternative positions and orientations of locking projection and locking recess that may be used to form further embodiments within the scope of the disclosed subject matter.

DETAILED DESCRIPTION

Figure 3:
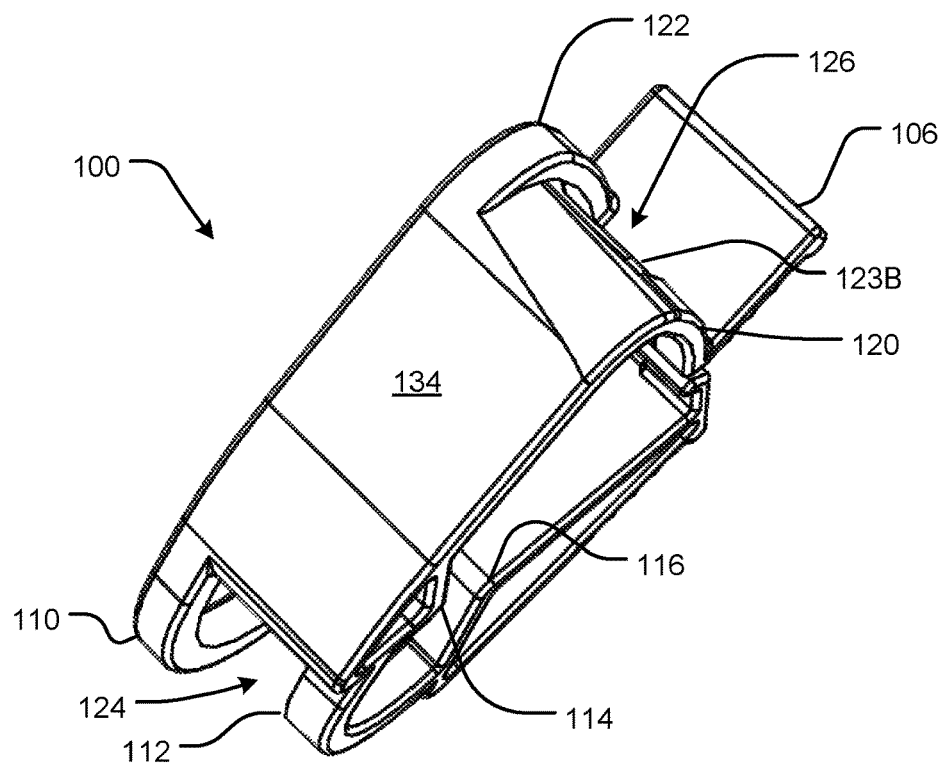
FIG. 3 shows the pinch clamp according to the embodiment of FIG. 2A from a third perspective showing a bottom surface that is opposite the first.

A pinch clamp is described which has an asymmetric configuration that allows it to have openings or recesses that face at angles relative to each other without defining overhangs that would prevent the pinch clamp from being released from each of the parts of a two-part mold. The pinch clamp consists generally of a strip that curves so that its ends can be brought together by manually squeezing the strip at its ends which oppose each other as a result of the strip curve. The strip ends contain locking edges or surfaces that cause the strip ends to interferingly engage with each other and lock together. The strip contains opposing pinching projections that pinch a tube positioned such that when the strip is manually squeezed at its ends, the pinching projections converge about opposite sides of the tube, thereby pinching the tube. A tube can be positioned between the pinching projections by running between openings in the strip.

A further feature of pinch clamp embodiments disclosed herein is that members on lateral sides of the openings are in an offset relationship such that opposing surfaces of each can be molded by opposite parts of a two-part mold. This feature is described with respect to two embodiments in relation to FIG. 6A.

By allowing pinch clamps to be molded by two-part molds, a high packing density of the pinch clamps can be achieved because they can be arrayed tightly, for example in a two-dimensional array such as a hexagonal or rectangular array, without leaving room for the advancement or withdrawal of additional mold parts in different directions. In addition, the complexity of the molding machinery and molding parts is reduced. Similar packing density advantages can be achieved using more than two parts but which retain an inherent property of the two-part mold in that the mold pieces can separate along a single path of separation. For example, see FIG. 6B and attending discussion for an example where more than two mold parts are used. In embodiments, the pinch clamp permits the use of mold parts that can release the pinch clamp without interference from overhangs, where the mold parts have multiple parts but each part belongs to a set that moves in a single direction (see the arrows labeled 211 in FIGS. 6A and 6B where parts 212 and 214 form a set and the two parts 212 and 214 can be released from the pinch clamp by moving relative to it in the same direction). Note that the mold parts do not necessarily have to move apart simultaneously. In every instance in the present disclosure of an embodiment where two-part mold is discussed, it is contemplated that one or both of the parts of the two-part mold part can be made up of several component parts to form further embodiments.

A further feature that may be provided in any of the disclosed embodiments is an anti-cross-clamping function. In embodiments, the anti-cross-clamping feature includes anti-cross-clamping edge or surfaces on each of the opposing ends of the strip that are shaped for mutual engagement such that when the strip is manually squeezed, the anti-cross-clamping edge or surfaces help to prevent the opposing ends of the strip from being out of alignment; in other words, the alignment of the opposing ends of the strip is corrected. In embodiments, this correction of the alignment occurs progressively as the strip is squeezed where at least two anti-cross-clamping edges or surfaces of one strip end are confined between at least two anti-cross-clamping edges or surfaces of the other strip end. In embodiments, two outward-facing edges or surfaces can be confined between two inwardly-facing edges or surfaces as the two strip ends are brought together due to pinching. An example of this anti-cross-clamping configuration is shown in FIGS. 7, 8, 16A, 16B, 16C, for example. This anti-cross-clamping configuration may be integrated in the configuration of any of the embodiments.

Another anti-cross-clamping feature that can be integrated in the configuration of any of the embodiments provides a single edge or surface on each end of the strip which oppose each other and are positioned such that when in contact, they permit the ends of the strip to be brought together progressively while the edges or surfaces are in engagement. While the anti-cross-clamping edge or surfaces are in engagement, the ends of the strip are in alignment.

The pinch clamp may further be provided with a lateral biasing feature such that the force of squeezing the pinch clamp also tends to urge the single edges or surfaces on each end of the strip laterally against each other. This may be provided by suitably configuring grip portions of the strip that are used to squeeze the pinch clamp. For example, the grip portions that are pushed against by manual squeezing may be angled or notched in such a way as to urge the ends of the strip laterally as well as toward each other, thereby to urge the anti-cross-clamping edges or surfaces on one of the strip ends against the other of the anti-cross-clamping edge or surfaces on the other of the strip ends. An example in which the grip portions are notched is shown and described in reference to FIG. 1B. Other asymmetric features such as fences that rise from edges or surfaces of the grip portions may also produce this lateral urging thereby to cause a similar effect as illustrated in, and described with reference to, FIG. 1C.

Another anti-cross-clamping feature prevents cross-clamping by disallowing locking. One or both of the locking edges or surfaces of the anti-cross-clamping feature that uses a single edge or surface on each end of the strip may be shaped such that the locking edges or surfaces cannot engage when the opposing ends of the strip are out of alignment. In use, if the pinch clamp is manually squeezed such that the single edges or surfaces on the ends of the strip are moved laterally away from each other such that they are out of engagement, the locking edges or surfaces will not engage. These two features may be combined, one in which the anti-cross-clamping edges or surfaces, one at each end of the strip, engage with lateral movement in one direction thereby guiding the ends together leading to alignment, and the other in lateral movement causes the locking edges or surfaces to fail to lock. Thus, the user may learn quickly to bias the grip portions laterally in the proper direction when squeezing the pinch clamp thereby to cause the single edges or surfaces on the ends of the strip to remain in contact with each other while the pinch clamp is squeezed. The feature when the locking edges or surfaces fail to lock may further be combined with that where lateral biasing feature such as fences, notches, or angled grip portions.

The term "alignment" is used here to describe the range of configurations where the pinching projections are mutually aligned to reliably pinch the tube therebetween. When out of alignment, or cross-clamped, the projections may fail to pinch the tube so as close the tube as expected, for example, to form a complete seal of the tube.

A pinch clamp of any of the embodiments disclosed herein may have the configuration of a curved strap with central openings between the strap ends. The openings between the strap ends may be sized to permit a flexible tube to be passed between them. The strap may have pinching projections that are positioned opposite each other so as to converge and pinch a tube passed between the openings when the strap ends are pushed together. The openings may be defined by legs that are offset relative to each other in a direction of a line running between the centers of the two openings (thus following the axis of a tube passed between the two openings). The offset may be such that the pinch clamp is releasable from a two-part mold without deformation.

Figure 15A:
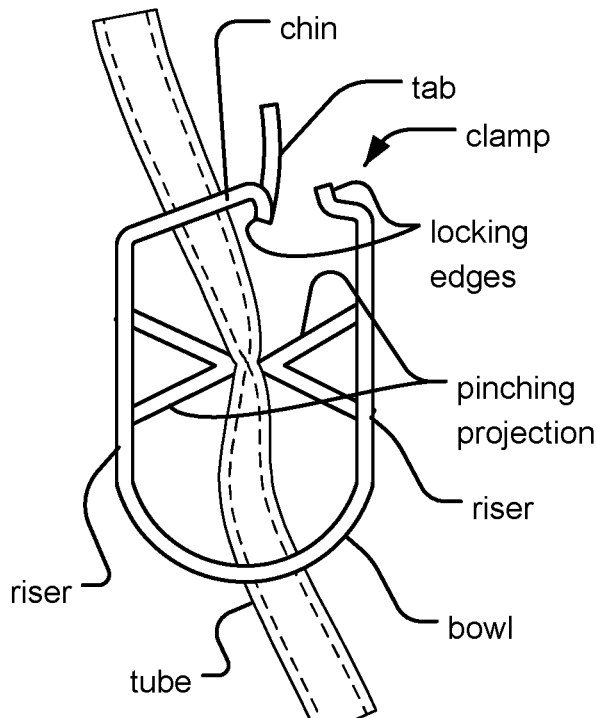
FIG. 15A illustrates a naming convention for identifying parts of a pinch clamp according to a generalized configuration.

FIG. 15A illustrates a naming convention for identifying parts of a pinch clamp applied to a particular embodiment, which is of a schematic form. The limitations from the diagram are not intended to be limiting of the meaning of the terms, but merely shows a schematic embodiment of a pinch clamp labeled according to the naming convention. In embodiments, a bowl portion is a portion of any configuration that is generally of the form of a strip shaped so that it has two riser portions extending toward respective ends of the strip that joins the riser portions. The bowl portion may be curved or straight. It joins respective ends of the riser portions such that they are at least sufficiently parallel that they can be squeezed together. Thus, the riser portions can form an acute or even oblique angle where they join the bowl portion, or they can be straight or curved or piecewise curved. One or both riser portions may provide a support location for at least one pinching projection and a surface that can be pinched. The bowl portion may also have an opening that helps to guide a tube to the one or more pinching projections and also helps hold the pinch clamp to the tube. A chin portion may form a portion between a strip and one of the riser portions that forms an angle with the proximate riser portion. The chin portion may have an opening that also helps to guide a tube to the one or more pinching projections and also help hold the pinch clamp to the tube. The locking edges or surfaces may be near the ends of the strip and may be of any form that allows the pinch clamp to be locked in a manually squeezed configuration. The release tab may be positioned anywhere, if there is one.

It can, for example, be located on either end of the strip. There may be more than one. It may provide the function of providing a grip for releasing the lock of the pinch clamp to allow fluid to flow through the tube. The strip does not need to be flat or uniform, but simply a member that can be piecewise or smoothly curved so as to bring two portions (riser portions) into sufficient relative position to allow them to be squeezed.

Figure 15B:
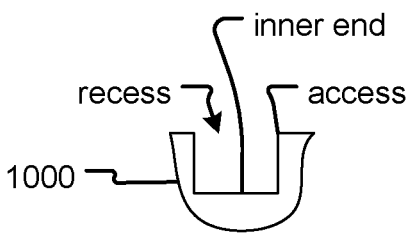
FIG. 15B defines feature of a recess.
Figure 15C:
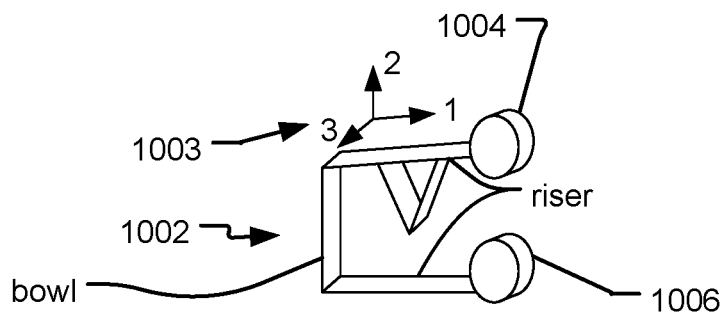
FIG. 15C defines directions relative to the general configuration of a squeeze clamp according to embodiments of the disclosed subject matter.

FIG. 15B illustrates an arbitrary part 1000 with a recess for purposes of defining the parts of a recess. The recess can be a trough or a pit or depression or other cavity and has an inner end opposite an access. The terms are defined in the drawing. The shape of the recess can be curved or faceted. FIG. 15C defines directions 1003 relative to the general configuration of a squeeze clamp 1002 according to embodiments of the disclosed subject matter. A first direction 1 is from the bowl portion to the locking portions 1004 and 1006 (which are indicated figuratively). The first direction 1 is generally a direction coinciding with the longitudinal axes of the riser portions. A second direction 2 points from one riser to the other and is generally aligned with the axis of a molding pin that forms the chin and bowl openings as well as the guide and receiving recesses of embodiments or the locking recess of other embodiments. A third direction 3 is normal to a plane through which the longitudinal axes of the depending riser portions both lie. The third direction 3 is also the direction (or parallel to that direction) of release of the pinch clamp from the major mold parts.

Referring to FIGS. 2A through 5, details of a particular configuration of a pinch clamp 100 are shown. The pinch clamp 100 is generally formed from a strip 109 with ends 109A and 109B carrying various features to permit a clamping of a tube without cross-clamping.

The pinch clamp 100 overall design including anti-cross-clamping aspects are provided in a configuration that lacks overhangs that would prevent the pinch clamp 100 from being released from the parts of a two-part mold. This property is provided despite the fact that the pinch clamp 100 has openings facing generally in different directions (such as openings 124 and 126 which face in at a roughly 90 degree angle relative to the facing directions of the major openings 136, 137, and 138 of the pinch clamp 100). Thus, the pinch clamp 100 has no overhangs and can be molded and released from the parts of a two-part mold without additional actions or mold pieces.

It may be confirmed by inspection that the general shape of the pinch clamp 100 further permits the use of positive draft angles to facilitate release of the molded pinch clamp 100. Since positive draft angles drawn to scale may be difficult to discern in a drawing, it may be confirmed by inspection that the configuration allows for surfaces with positive draft angles and no overhangs.

The pinch clamp 100 also has an anti-cross-clamping feature which includes a locking projection 102 with an anti-cross-clamping surface 107A that engages a complementary anti-cross-clamping surface 107B on a guide 104 of member 120 of strip 109. The anti-cross-clamping surfaces 107A and 107B face in opposite directions and may be formed by opposing surfaces of respective two-part mold parts.

The pinch clamp 100 strip 109 has opposing pinching projections 114 and 116 on upper 132 and lower 134 riser portions of the curved strip 109 to pinch a tube when placed so that it runs through the openings 124 and 126. The upper 132 and lower 134 riser portions of the curved strip 109 are joined by bowl members 110 and 112 which define the opening 124. The strip 109 is further extended to define a chin portion 139 by members 120 and 122 which also define the opening 126. As may be seen, the bowl members 110 and 112 are offset to allow the pinch clamp to be released in directions 111 from the parts of a two-part mold. As may be seen, the members 120 and 122 are also similarly offset to allow the pinch clamp to be released in directions 111 from the parts of a two-part mold. Also, it can be confirmed by inspection that the configuration of the pinch clamp 100 can include a suitable draft to facilitate release of pinch clamp 100 from the respective mold parts. This is because the entire configuration has no overhangs as viewed from opposite sides of directions indicated at 111.

Locking projection 102 has a locking edge or surface 123A that fits under a release tab 108 to engage with locking edge or surface 123B to case interfering engagement of the locking projection 102 with the release tab 108 when locking projection 102 is aligned with the opening 126 (i.e., the locking edges or surfaces 123A and 123B are aligned) to lock the strip 109 ends 109A and 109B together thereby to pinch a tube between the pinching projections 114 and 116.

A release tab 106 extends away from the bowl members 110 and 112 presenting a grip surface 115 which can be pressed to force the locking edges or surfaces 123A and 123B out of engagement and thereby release the pinch clamp 100. Thus, the locking projection 102 may be withdrawn from engagement under the release tab 108 by flexing the pinch clamp. Guide 104, which, in the present configuration, extends from the member 120, presents the anti-cross-clamping surface 107B for aligning the locking projection 102 by engaging with-cross-clamping surface 107A, thereby aligning the locking projection 102 with the opening 126 so that the locking projection 102 fits under the release tab 108.

An example of the anti-cross-clamping feature that disallows locking is illustrated by the present embodiment. Here the locking projection 102 retreats sufficiently away from the release tab 108 on the side of the projection that is adjacent the guide 104 to prevent the projection from catching on the release tab 108 remote from the guide 104 if the upper riser portion 132 is pushed such that the locking projection 102 is moved out of alignment with the opening 126 in the direction from member 120 toward member 122. This shape can be rendered as a chamfer 103 but the function can achieved with a variety of shapes and features which have the effect that the locking edge or surface 123A of the locking projection is angled away from the locking edge or surface 123B of the release tab in a direction remote from the anti-cross-clamping surfaces 107A and 107B. For example, in another variation, a projection on release tab 108 that faces the upper extent may force the locking projection 102 away from the release tab when it is aligned away from the opening 126. The locking projection may have a guide surface 121 that is inclined to push the release tab 108 on the chin portion 139 away from upper riser portion 132 when the pinch clamp 100 is manually squeezed.

Figure 14A:
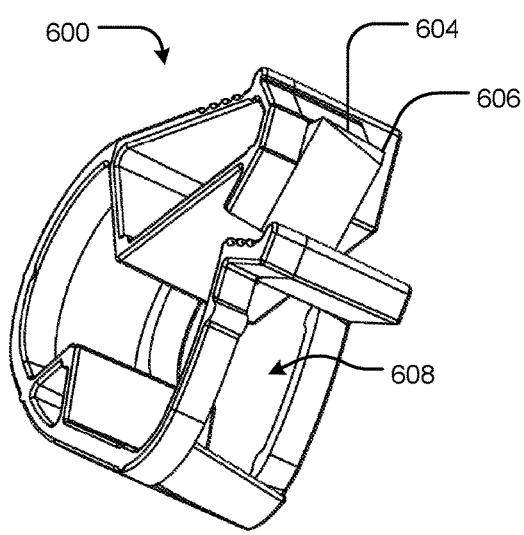
FIGS. 14A and 14B show respective views of the pinch clamp of FIGS. 13A and 13B to illustrate anti-cross-clamping features thereof, with FIG. 14B showing a closed configuration of the pinch clamp which closes by flexing.
Figure 14B:
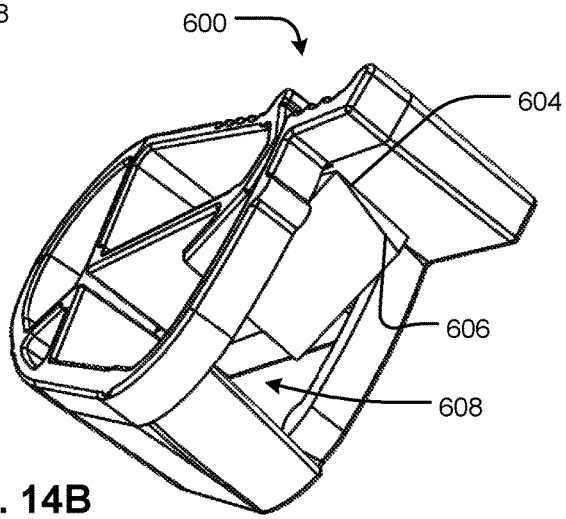

It can be seen in FIG. 14B how the locking projection 102 fits within the opening 126. This embodiment, though somewhat different, shows a similar embodiment with a projection 604 fitting into an opening 608 in a manner that is essentially the same as the fit of the locking projection 102 into the opening 126. This shows how the release tab 606 forms a locking edge or surface, as locking edge or surface 123B, to engage with the locking projection 604 (similar to 102).

Figure 4:
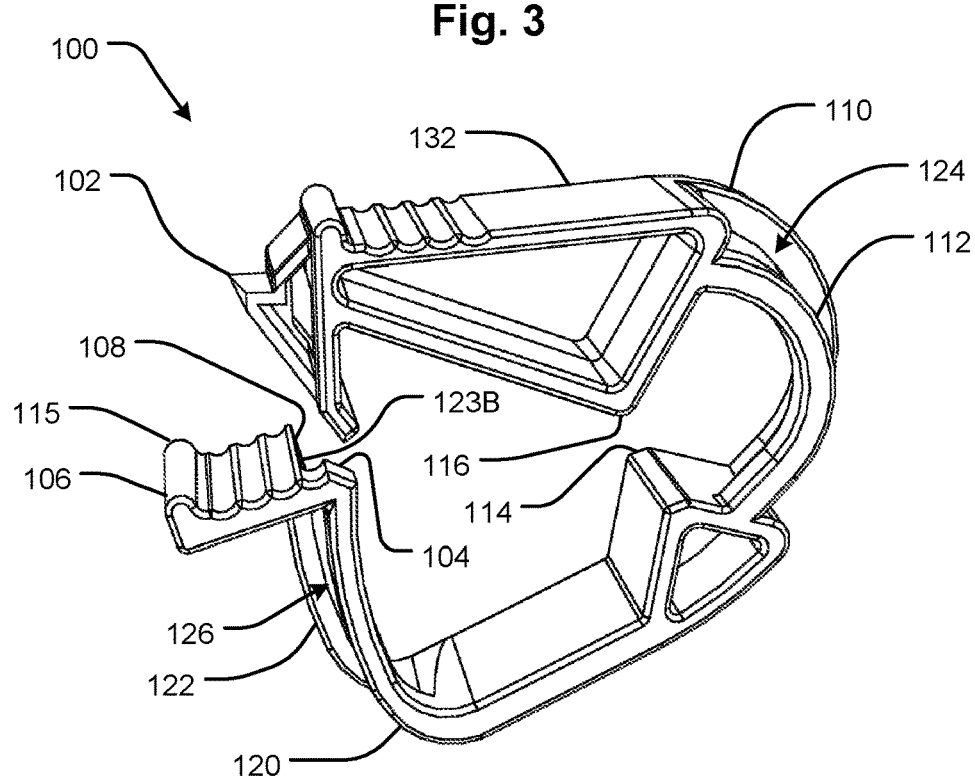
FIG. 4 shows a side view of the embodiment of FIGS. 2A and 2B.
Figure 5:
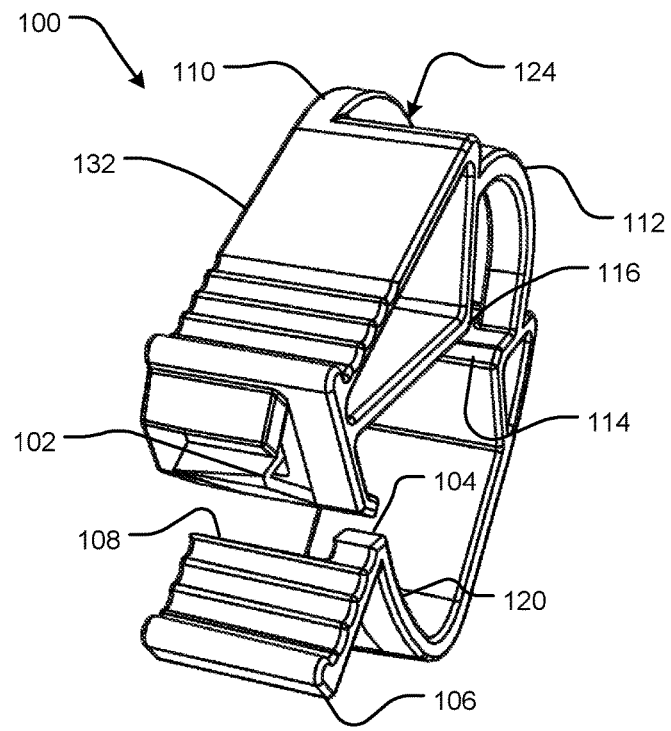
FIG. 5 shows a front view illustrating engagement and asymmetrical features of the embodiment of FIGS. 2A and 2B.
Figures 6A, 6B:
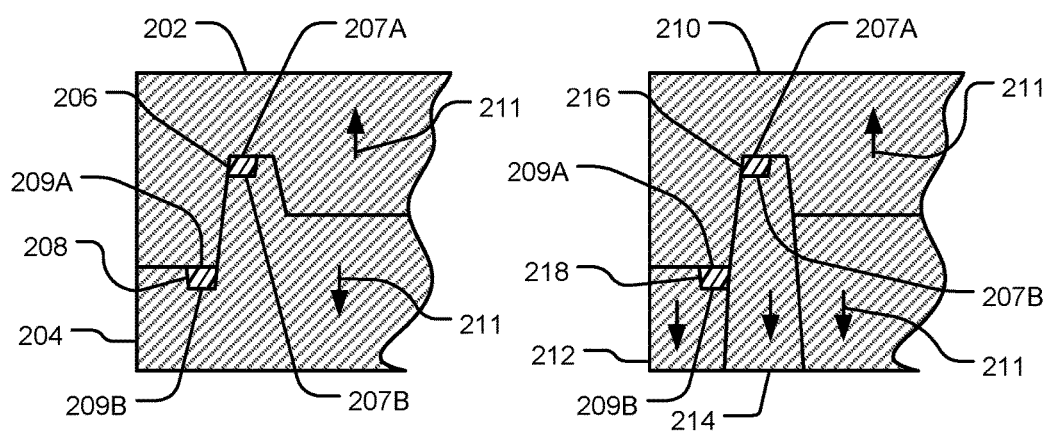
FIGS. 6A and 6B show mold interfaces in section to illustrate how the end opening of the pinch clamp can be formed from two (FIG. 6A) or three (FIG. 6B) mold parts. In both cases, the mold parts converging and separating to release the molded part in a simple fashion, for example, separating along a common line in opposite directions (open and close mold).

It can be seen in FIG. 4 (and the other figures) how the members 120 and 122 and bowl members 110 and 112 are offset facilitate release from mold parts. FIG. 6A illustrates a section view of a pair of mold parts showing figuratively how the offset of the members 120 and 122 and bowl members 110 and 112 allows them to be release from mold parts. The mold parts are indicated at 202 and 204. The molded parts illustrated by members 206 and 208, which are offset in a direction perpendicular to the release directions indicated by the arrows at 211. It may be noted that opposing surfaces 207A and 207B of member 206 are formed by the opposite mold parts 202 and 204, respectively. It may also be noted that opposing surfaces 209A and 209B of member 208 are formed by the opposite mold parts 202 and 204, respectively. Thus, it may be confirmed by inspection that the offset relationship of the members 206 and 208 allows this and thereby permits an opening for admission of a tube to be formed in two-part mold. FIG. 6B shows an alternative configuration that uses additional parts including a pin 214 and major parts 210 and 212 to form members 216 and 218. In both cases a stepped parting line is provided to facilitate manufacture of the molds, but major steps are not inherent in forming molds for the asymmetric configuration of pinch clamp 100.

A pinch clamp of any of the embodiments disclosed herein may have the configuration of a curved strap with central openings between the strap ends. The openings between the strap ends may be sized to permit a flexible tube to be passed between them. The strap may have projections that are positioned opposite each other so as to converge and pinch a tube passed between the openings when the strap ends are pushed together. One strap end may have a locking projection and the other strap end may have a locking recess through which the projection may pass when the strap ends are properly aligned so as to prevent cross-clamping. When the locking projection and locking recess are aligned and the locking projection is passed through the locking recess, the locking projection can form a locking engagement with the locking recess, thereby pinching a tube passed between the pinching projections. The locking recess may be sized relative to the locking projection such that the locking projection is excluded and thereby prevented from forming a locking engagement with locking recess. The locking projection and/or the locking recess may be tapered so as to capture and progressively move the locking projection and locking recess into alignment as the pinch clamp is squeezed. In embodiments, the locking recess can be continuous with one of the central openings, essentially defining an extension of the one of the central openings. As such, the locking recess and opening can both be molded using a mold cavity and a pin, the pin defining the central opening and locking recess.

In a variation of the foregoing pinch clamp embodiments, a major edge or surface of a locking projection major surface serves as the locking edge or surface of the locking projection. Essentially this allows the same major structure to perform both the locking and guiding functions. See for example, the major surface 309 of the locking projection 304 of the embodiment 300 and the surface of locking projection 702 bounded by locking edge or surface 703A in embodiment 700. A concomitant feature of these embodiments is that a projection is provided which guides the ends of the strip toward each other in alignment and the full edge or surface of this same projection serves as the locking edge or surface to engage a locking edge or surface on the chin of the pinch clamp.

Figure 7:
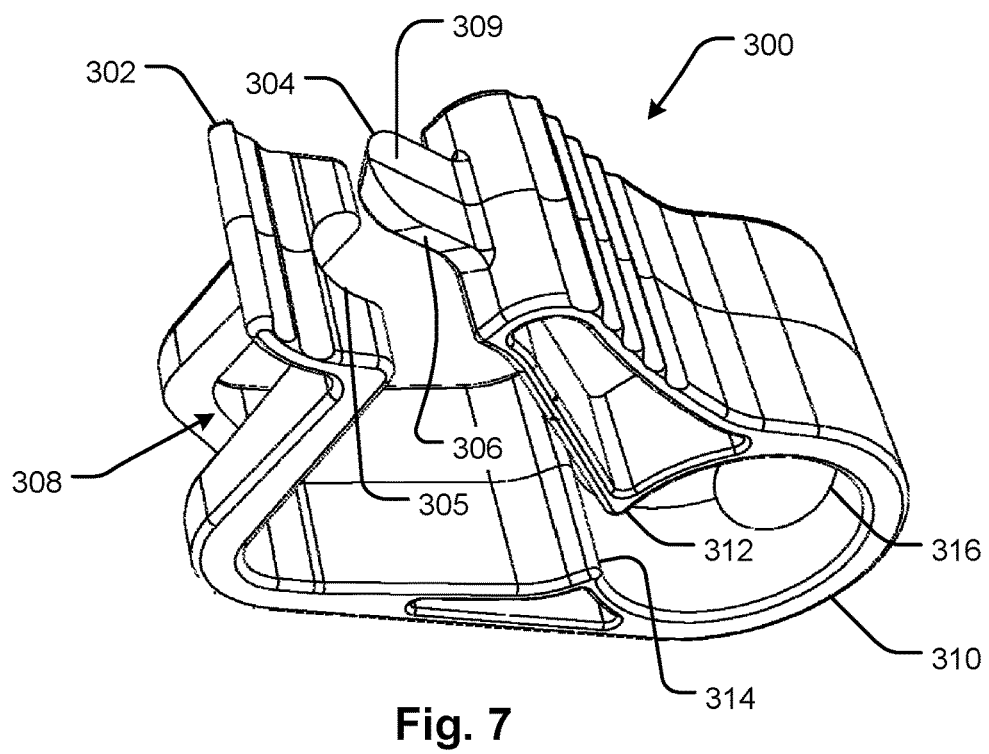
FIGS. 7 and 8 show a pinch clamp with anti-cross-clamping features from respective perspectives.
Figure 8:
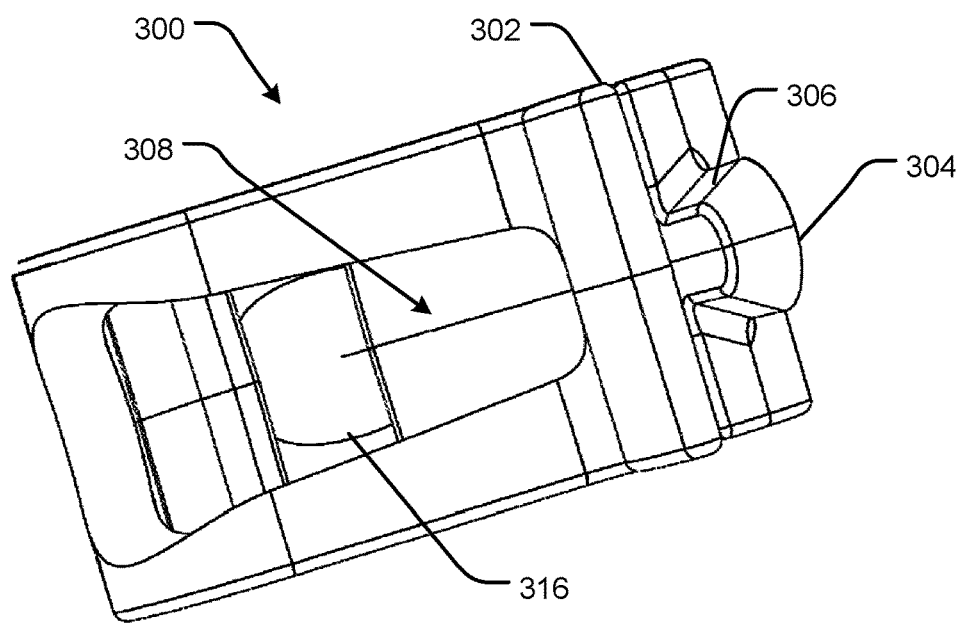

FIGS. 7 and 8 show a pinch clamp 300 that conforms to the immediately foregoing embodiments. A pinch clamp 300 has symmetric openings 308 and 318 and other features that may be formed by more conventional multiple component or action molding components or techniques. A projection 304 has a tapered surface 306 that fits into a locking recess 305 that is continuous with the opening 308. The tapered surface 306 helps to capture and progressively move the locking projection 304 into alignment with the locking recess 305 as the pinch clamp 300 is squeezed. The opening 308 and recess 305 are continuous and shaped such that they can be molded with a pin and two-part mold. The opening 315 can be molded in the same way. See FIG. 20A for illustration of the molding arrangement. The opening 308 permits the passage of a tube. A release tab 302 provides a manual grip surface to facilitate release of the pinch clamp after locking. The locking projection 304 fits into the opening 308 to lock under the release tab 302. The openings 308 and 316 allow a tube to pass between them and through them so that the tube lies between pinching projections 312 and 314 which pinch the tube when the pinch clamp 300 is manually squeezed.

Figures 11, 12:
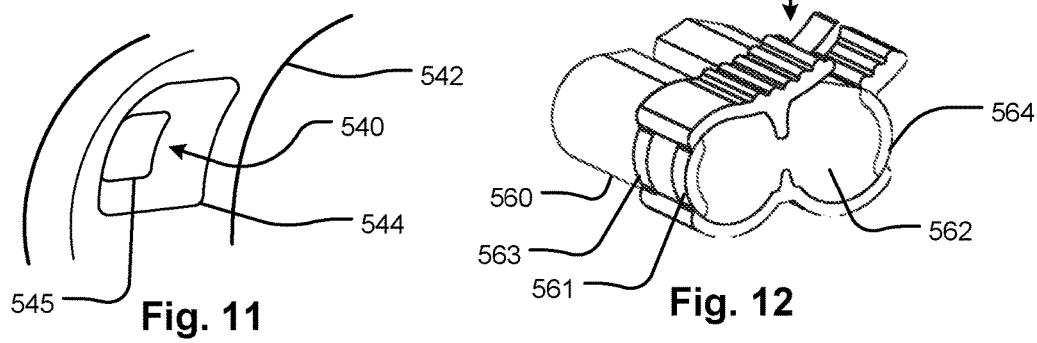
FIG. 11 shows a chamfered tube-receiving opening in a clamp part to facilitate pre-assembly of tubing sets with pinch clamps that may be used with any of the embodiments of pinch clamps and as a feature of further embodiments of the prior art and the disclosed subject matter.
Figure 13A:
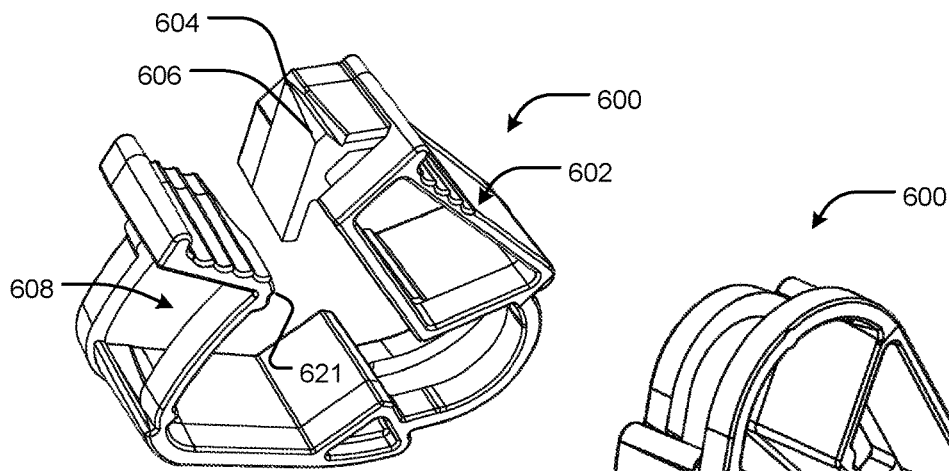
FIGS. 13A and 13B show respective views of another pinch clamp.
Figure 13B:
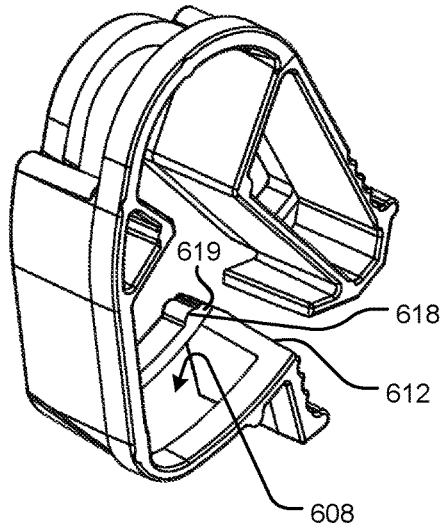

A pinch clamp of any of the embodiments disclosed herein may have the configuration of a curved strap with central openings between the strap ends. The openings between the strap ends may be sized to permit a flexible tube to be passed between them. The strap may have pinching projections that are positioned opposite each other so as to converge and pinch a tube passed between the openings when the strap ends are pushed together. The configuration may be such that the openings between the strap ends face in directions that form an angle of 90 degrees to open sides of the strap (e.g., see open sides 518 and 520 of pinch clamp 500 described below) thereby defining overhanging portions coinciding with the openings. In a method of molding such pinch clamps, molding pins may be used. A first pin has recesses that define the strap portions with a respective opening and fits partly within a second pin that forms further portions of the strap. In the method, after the pinch clamp is formed, the second pin is withdrawn axially from the first pin freeing the first pin to release the strap portions that define the respective opening. This mold and method is illustrated by the example of FIG. 12 described in more detail below.

Figures 9A, 9B:
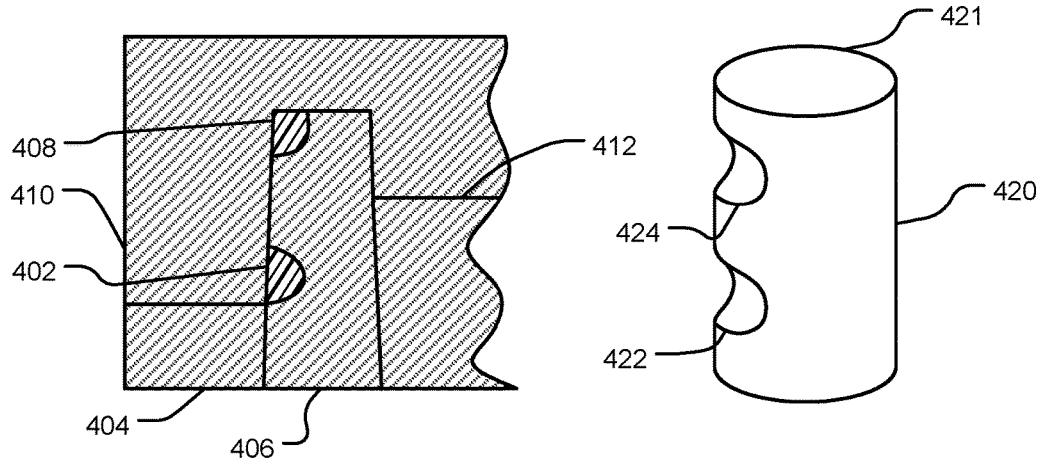
FIGS. 9A and 9B show features for an open and close mold design that employ pop-out recesses in pins to permit tube-receiving openings and other features to be formed by the mold.
Figure 10:
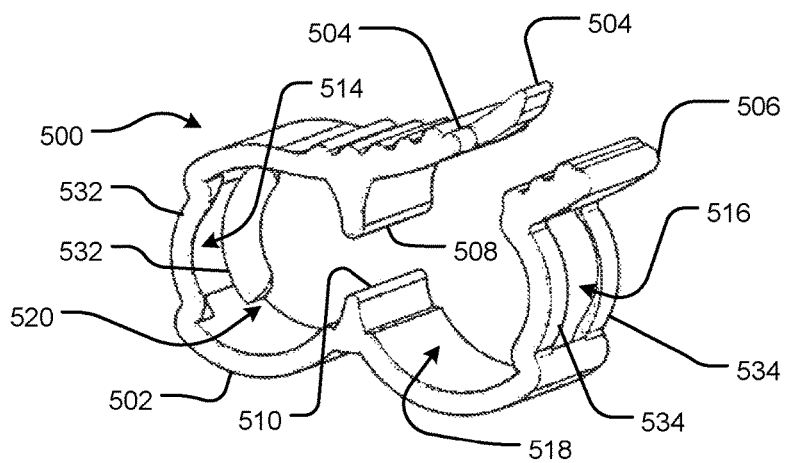
FIGS. 10 and 12 show further features for an open and close mold design that employ pop-out recesses in pins to permit tube-receiving openings and other features to be formed by the mold.

FIG. 9A illustrates a molding configuration that may be used to mold a configuration as shown in FIG. 10 which allows a single action molding operation in which overhang features 402 and 408, corresponding to members 532 and 534, to be released from a pin 406 after the extraction of the molded pinch clamp 500 from mold parts 404 and 410. A stepped parting surface 412 may be used or not depending on how the mold parts are manufactured. By stepped it means that the interfacing surfaces of the major mold parts are not coplanar, thus defining a step, as illustrated at 412 and 404 which are interfacing surfaces. FIG. 12 shows pin embodiments that may be used to form the pinch clamp 500 in a molding operation. A large mold pin 562 is inserted in an opposing direction relative to pins 560 which have recesses for forming the members 561 and 563 and corresponding members, one of which is indicated at 564, of the pinch clamp 500. The pin 562 can be removed from pins 560 after the pinch clamp is molded allowing the pins 560 to be moved laterally to release the members 561, 563, and 564. The pinch clamp 500 has pinching projections 508 and 510 that pinch a tube passed between openings 514 and 516. The pinch clamp open sides 518 and 520 are generally cylindrical and may be formed using the pin-based molding method described above.

The pinch clamp 500 has a locking projection 504 that fits within opening 516 and engages under the release tab 506 after passing through the opening 516. If the locking projection 504 is out of alignment with the opening 516 such as would allow cross-clamping, the locking projecting 504 finds no edge or surface with which to engage since it cannot enter the opening 516. This prevents cross-clamping by the pinch clamp 500.

FIG. 9B shows another molding pin 420 configuration in which the recesses 422 and 424 are located remote from the tip 421 of the pin 420 as opposed to having one of them located at the tip as in the embodiment of FIG. 9A.

FIG. 11 shows a feature that may be used in any of the disclosed embodiments or prior art pinch clamps 542, namely, a progressively narrowing opening 540 that forms a guide for inserting tubing during assembly of parts, such as tubing sets, employing the pinch clamp. The opening gradually reduces from an entrance 544 to an exit 545 thereby guiding the tip of a tube inserted through it into the opening 545.

FIGS. 13A through 14B show an embodiment of a pinch clamp 600 that is similar to embodiment 100 of FIGS. 1 through 5. The features of pinch clamp 600 are mostly the same as in the pinch clamp 500. The upper extent 602 has a deeper cross-section that facilitates release and provides more rigid support of the locking projection 604. Also, a bump 618 helps to guide the locking projection 604 during squeezing by extending the guiding surface 619 that engages with the locking projection 604 during squeezing of the pinch clamp 600. The bump 618 also pushes the locking projection away from the opening 608 if the locking projection 604 is not aligned properly with the opening 608 thereby to prevent catching of a portion of the locking projection 604 in a non-aligned position. The chamfered portion 606 prevents the locking projection 604 from locking when the locking projection 604 is laterally displaced away from the guiding surface 619. FIG. 14B shows the locking projection 604 engaged and within the opening 608.

FIGS. 16A-16C shows a symmetric pinch clamp 700 includes a locking projection 702 with a locking edge or surface 703A that engages a locking edge or surface 703B defined under a release tab 716. The locking projection 702 may be tapered as shown at 704 so that it fits into a locking recess 706 in the release tab 716 as the pinch clamp 700 is squeezed. There is also a beveled surface 705 that flows into a forward surface 707 of the locking projection 702 to prevent interference as the pinch clamp 700 is manually squeezed. The locking projection 702 is shaped to stay within the locking recess 706 and thereby hold the ends of the strap forming the pinch clamp 700 in alignment so that the pinching projections 712 and 721 do not cross-clamp a tube running between the openings 710 and 712 as the pinch clamp 700 is manually squeezed. After squeezing, the locking edges or surfaces 703A and 703B interferingly engage to lock the pinch clamp closed. Note that the ring 717 under the release tab 716 is a slight indentation produced by molding as will be evident from the further discussion below.

Figure 18A:
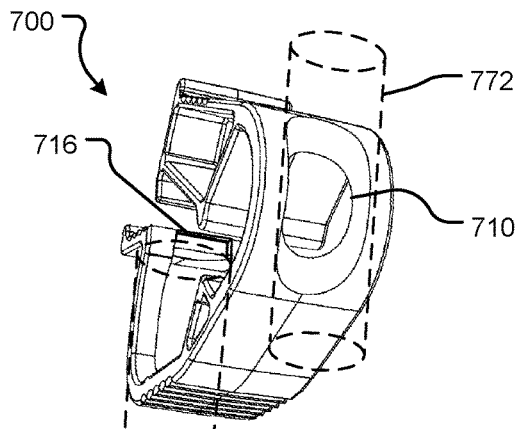
FIGS. 18A, 18B, and 18C show mold elements that may be used to make the pinch clamps of FIGS. 16A, 16B, and 16C, and features and variations thereof, as well as other pinch clamp embodiments.
Figure 18C:
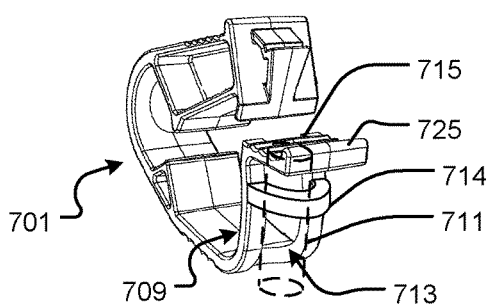

Referring also to FIG. 18A, the release tab 716 may be formed in part by a pin 730 in a molding process as can be confirmed by inspection, for example, see the circular indentation 717 and the cylindrical notches defining the bowl 710 and chin 712 openings. Also note the locking recess 706 may be formed by extension 732 of the pin 730. The bowl opening 710 may also be formed by a pin 772 as illustrated. Referring to FIG. 18C, which shows a pinch clamp 701, it is possible for the chin opening 713 to be separate from the locking recess 715 while still being capable of molding in the manner described, that is, using a two-part mold with two pins as explained with reference to FIG. 18A. In the embodiment shown, a bridge 714 may be formed in part by the two-part mold and in part by a pin 711. The bridge 714 separates and can provide support to the chin portion 709. The bridge 714 may be arranged to extend outwardly as shown or it may extend inwardly on an opposite side of the chin portion 709 in an alternative configuration. Further, the bridge 714 may have other outer shapes such as rectangular rather than the outer cylindrical shape illustrated.

A release tab 725 may be used to disengage the projection 702 to open the pinch clamp 700. The locking recess 715 is rectilinear in shape. A second cylindrical pin can form the opening in the middle of the pinch clamp 700 as can be seen at 710. The pins can be arranged to move in parallel fashion during molding as may be confirmed by visual inspection of the pinch clamp 700.

As a result of the anti-cross-clamping function of the locking projection and locking recess 702 and 706, a savings in material may be obtained because the configuration does not require as much stiffness to avoid cross-clamping as would be required to discourage cross-clamping. This is because the locking projection and notch reliably prevent cross-clamping. Also, the configuration shown at 700 can be formed with a two bilaterally symmetric mold halves and two pins and so can be formed at relatively high density in a simple mold setup. Note that the pins can be shared by two or more pinch clamps by suitable layout of the pinching clamps.

Figure 17A:
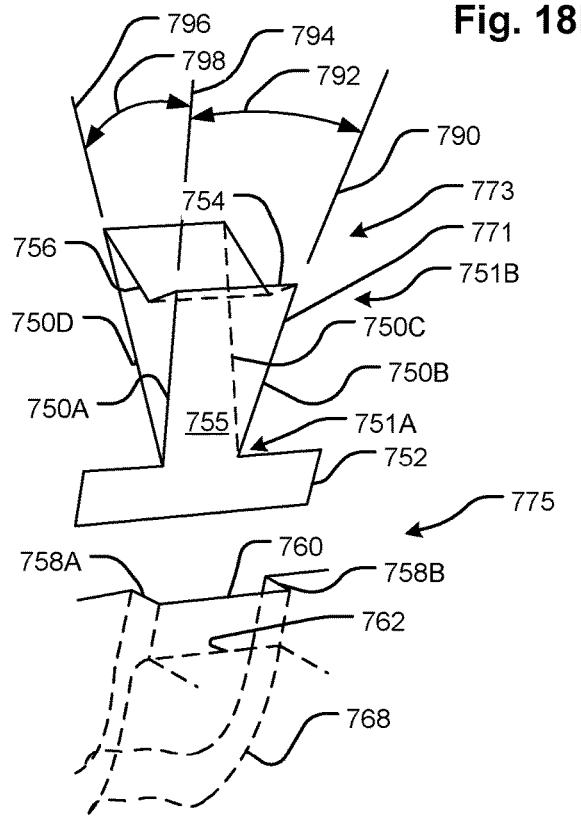
FIG. 17A shows details and variations of the anti-cross-clamping portions of the pinch clamp of FIGS. 16A, 16B, and 16C.

FIG. 17A highlights features of the anti-cross-clamping configuration of the pinch clamp embodiment 700 and other embodiments. Note that these features may form a part of any pinch clamp formed generally as a strap in which the strap ends lock together and create a potential susceptibility to cross-clamping of a tube. A rectangular-shaped locking recess 760 is formed in one end 775 of a strip while a locking projection 771 of rectangular shape is formed on the other end 773 of the same strip. The locking recess 760 defines a locking edge or surface 762 which engages with a locking edge or surface 754 of the locking projection 771. The locking projection 771 tapers from a small leading end 751A to a larger trailing end 751B so that it is generally of a pyramid shape with edges or surfaces 750A and 750B diverging at angles 792 in a lateral axis and diverging in a forward axis from edge or surface 750C and 750D by an angle 798. A beveled surface 752 flows without a step or other interruption into a forward surface 755 of the locking projection. In embodiments, the beveled surface 752 is coplanar with the forward surface 755. The beveled surface 752 provides a transitional guide so that a user can align the ends of the strip so that the leading end 751A of the locking projection 771 can be aligned with the locking recess 760 and the edges or surfaces 750A and 750B is interferingly engaged by the edges or surfaces 758A and 758B so that the locking projection 771 is captured by the locking recess 750 by interfering engagement thereof. The beveled surface also eliminates any step or other interfering element that would otherwise prevent preventing the locking projection 771 leading end 751A from smoothly moving into the locking recess 760 during squeezing of the pinch clamp. The chin opening 768 is continuous with the locking recess 760 as discussed. As illustrated by examples, the locking projection can be shaped as a pyramid or a cone or other tapered prism shape so that it progressively centers the locking edge or surface thereof with respect to an opening with the locking edge or surface with which the projection locking edge or surface interferingly engages to lock the riser portions together.

Figure 17B:
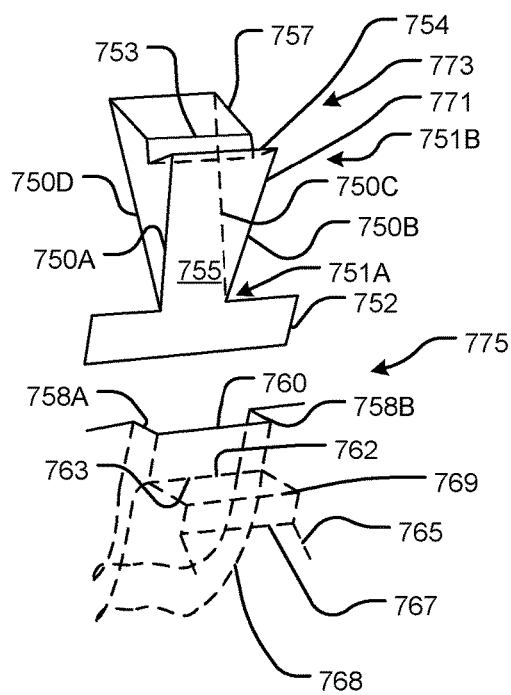
FIG. 17B illustrates a feature that generates a double clicking haptic feedback to the user.

Referring to FIG. 17B, the locking projection 771 of any of the embodiments may be configured with a step or other edge-bearing element effective to create a secondary haptic clicking or snapping sensation and/or sound during closing. The secondary feedback follows the initial feedback caused by the locking projection slipping into the chin opening as the forward edge of the locking projection edge or surface passes a recess edge 763 and slips forward into the opening. This is the first haptic response. Then, as the pinch clamp is pinched further, the locking projection 771 extends into the chin opening so that a rear portion 757 slips into the chin opening beyond a step edge 753 and when the user begins to release the pinching force, the recess edge 763 adjacent the step edge 753 slips over the step edge 753 releasing the residual spring force left in the pinch clamp to cause the locking edge or surface 754 to accelerate until stopped by the locking recess locking edge or surface 762, thereby generating the audible or tactile feedback to the user. This provides the function of confirming a full engagement of the pinch clamp. This particular configuration may be applied to any of the described embodiments herein to form new embodiments. Further other mechanisms for generating the same or similar haptic feedback during release can be provided to form new variations of the disclosed embodiments. Thus, the surface 757 defines an initial landing surface angled such that when it engages the edge 763, the latter rides the surface until it falls off the edge 753 and lands on the locking edges or surfaces 754 and 762 engage. The double click haptic feedback can also be accomplished in other ways as well. A sloped surface 786 behind the chin locking edge or surface 762 may provide such an initial landing surface 765 that is sloped and which leads to a step between edges 767 and 769 that causes a similar effect in which the very edge of edge or surface 754 rides the initial landing surface 765 until it drops to the chin edge or surface 762. The initial click in this case would be the same as the embodiment described above, namely the locking projection 771 snapping into the opening after passing the edge 763 upon squeezing. These are two of a class of embodiments in which a first end of a strip forming a pinch clamp has two landing surface, a first which is sloped and which leads to a step which in turn leads to a second landing surface. The second end of the strip has a locking surface that and edge of the first landing surface and rides it until it falls off the step finally to engage the second landing surface. The engagement with the second landing surface is effective to retain the pinch clamp in its clamped configuration.

All of the embodiments described herein may be embodied as non-reopenable (once pinched it would stay pinched and cannot be released readily) or reopenable (in other words, disengaging, disengageable, releasable) pinch clamps. Reopenable pinch clamps are distinguished by having a release component such as the release tab 106, 302, 506, 716 of foregoing embodiments, usable to disengage the locking edges or surfaces and thereby permit a tube to be opened and closed selectively at different times. Any kind of manually actuatable element would be effective. In embodiments generally of the curved strip configuration, disengagement may be performed using a release mechanism such as a release tab that allows a user to move the locking projection relative to the locking recess so as to separate the mutually engaged locking edges or surfaces thereby to permit the ends of the strip to separate and allow the pinching projections to separate and unpinch the tube. In embodiments, the release mechanism includes a locking edge or surface of a single member with a single grip surface that moves as a unit to allow a user to release engagement easily without having to engage multiple surfaces or move multiple independently movable elements. Known locking clamps of the prior art have more than one element that would have to be moved making it difficult to open such a device with a single hand. Also non-reopenable pinch clamps are generally configured such that the force required to disengage, or the configuration required to disengage is difficult for a user to generate. A configuration amenable to single handed operation of the release mechanism would be one where the release grip is a single member that moves in unison (as distinguished from, for example, a device with two prongs that do not necessarily move well together if one is moved). Further, embodiments may also include the feature of providing fully closed openings in the chin and bowl portions so that a tube may be threaded therethrough and reliably maintained in position between the pinching projections to be pinched by the pinching projections without risk of being only partly pinched or unpinched when the pinch clamp is manually squeezed. Further, embodiments may also include the feature of being formed of a single unitary structure such that it can be molded of a single piece of plastic. Thus, in these embodiments, all the elements of the pinch clamp are integrally connected.

A further feature of embodiments is that the locking edges or surfaces are configured so as to make it practically impossible to cross-clamp. If a strip end is moved laterally in either direction and out of alignment, there is no portion of the engagement edges or surfaces or any other edges or surfaces that can lock the two strip ends together. This facilitates safety when experienced users operate the clamp without careful observation or even without looking at or confirming a state of the pinch clamp by touch. In embodiments, this function may be provided by the configuration where one of the portions of the pinch clamp that provides an anti-cross-clamping function by guiding the two strap ends together while maintaining alignment of the pinching projections, for example the locking projection, also supports one of the locking edges or surfaces. Also, the function is facilitated where the locking edge or surface carried by the locking projection cannot interferingly engage the locking edge or surface of the other end of the strip without this locking edge or surface being positioned within the locking recess which also serves to guide the locking projection. Thus, as can be confirmed by inspection of example embodiments, if a user inadvertently moves the locking projection away from the locking recess, the locking edge or surface carried by the locking projection cannot find the other engagement edge or surface in order to lock.

A further feature of the disclosed embodiments is that the pinch clamp is naturally in a U-shape without any configuration steps. The strip may be curved with the riser portions, which are used for manually squeezing the pinch clamp, substantially opposite each other around the tube without any interconnection of the riser portions, such as interfering engagement, being necessary to maintain this configuration. Thus, no initial set up is required to place the pinch clamp in a configuration where it is ready for pinching a tube other than positioning it on the tube, for example by threading the tube through openings in the bowl and chin portions of the strip. Thus, the pinch clamp of the latter embodiment can be removed from the mold, threaded onto a tube, and then operated without further configuration changes. Another way to put it is that the generally U-shaped structure of the pinch clamp retains its shape such that the first and second risers are in a configuration to allow them to be manually squeezed together with a pinching action without being held by an interconnection between said first and second riser portions.

Figure 19A:
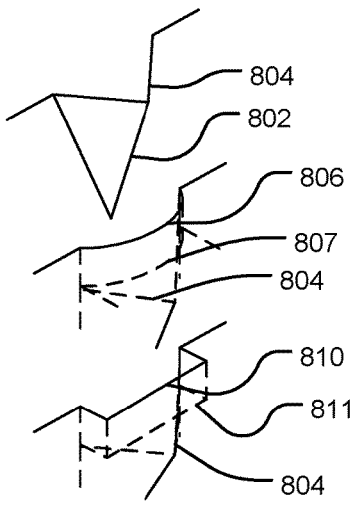
FIGS. 19A and 19B show respective alternative anti-cross-clamping portions that may be used to form additional variations of the pinch clamp of FIGS. 16A, 16B, and 16C.
Figure 19B:
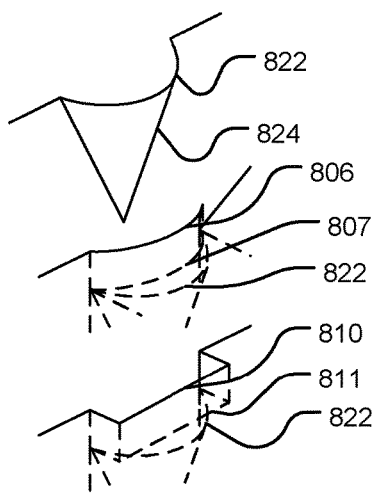

FIGS. 19A and 19B illustrate variations on the shapes of the locking edges or surfaces, recesses and projections. In FIG. 19A, a locking projection 802 has a triangular locking edge or surface 804 that may be guided by a rectangular 810 or curved 806 locking recess each with a correspondingly shaped locking edge or surface indicated respectively at 807 and 811. The locking recess and edge or surface may also be triangular but may have a locking edge or surface that is shallower so as to be capable of engaging the projection locking edge or surface 804. In FIG. 19B, a curved locking projection 824 has a rounded locking edge or surface 822 that may be guided by a rectangular 810 or curved 806 locking recess each with a correspondingly shaped locking edge or surface indicated respectively at 807 and 811. The locking recess and edge or surface may also be triangular but may have a locking edge or surface that is shallower so as to be capable of engaging the projection locking edge or surface 822.

Figure 18B:
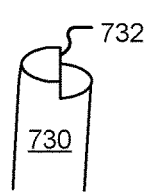
Figure 20A:
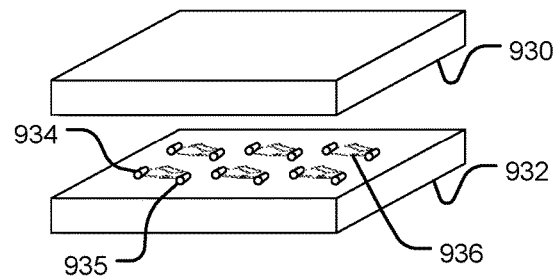
FIGS. 20A and 20B illustrate concepts related to the mold-facilitating features of the pinch clamp embodiments disclosed in the present application.
Figure 20B:
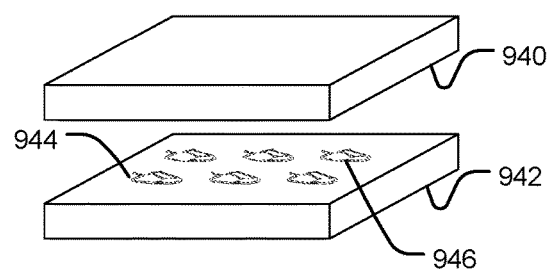

FIG. 20A shows how pinch clamp embodiments can be arrayed in a mold with pins to form the strip openings. FIG. 20B illustrates how pinch clamp embodiments of the asymmetric configuration can be arrayed in a two-part mold without pins. Mold parts 930 and 932 have recesses 936 defining respective portions of a pinch clamp and pins 934 and 935 defining bowl and chin openings in the pinch clamp strip. Note the pin defining the chin opening may also be used to define the locking recess for example as illustrated in FIG. 18B. The asymmetric pinch clamp embodiments may be formed in two-part molds (parts 940 and 942) without the use of additional components such as pins because the locking features and chin and bowl openings can be defined by offset parting lines in the mold parts 940 and 942.

FIGS. 22, 23A and 23B illustrate embodiments for making a pinch clamp generally of the type described in the embodiments of FIGS. 16A, 16B, 16C, and 18A. Mold parts 968 and 970 are held together to form molds for pinch clamps. Areas 960 and 962 are shown enlarged in FIGS. 23A and 23B, respectively, each showing recesses for four pinch clamps. The recesses for one pinch clamp are indicated at 983 and 984. Supports 989 and 990 hold pins 978, 979, 980, and 981 which fit into channels 977, 976, 987, and 988, respectively to form the chin and bowl openings of respective pinch clamps. Chassis alignment pins 973 and holes 975 for receiving them may be used. The pins 980 and 981 may be configured to form the locking recess of the pinch clamps as described in reference to FIG. 18A including variations of other shapes of locking recesses also described herein.

Figure 21A:
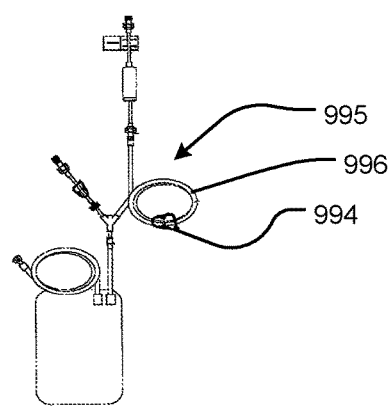
FIG. 21A shows a medical treatment fluid circuit set with tubing having attached thereto at least one pinch clamp according to the disclosed embodiments.
Figure 21B:
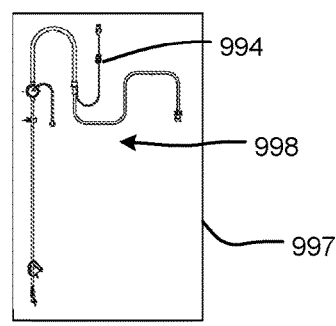
FIG. 21B shows a medical treatment fluid circuit with at least one pinch clamp according to the disclosed embodiments stored in a sterile package, such as a plastic envelope.

FIG. 21A shows a medical treatment medical treatment fluid circuit set with tubing having attached thereto at least one pinch clamp of the embodiments described herein. A fluid circuit set 995 has tubing portions 996 with at least one pinch clamp 994 according to embodiments described herein. FIG. 21B shows a medical treatment fluid circuit with at least one pinch clamp stored in a sterile package, such as a plastic envelope. A fluid circuit set 998 with at least one pinch clamp 994 attached thereto is stored in a sealed sterile container 997 such as a plastic bag. The pinch clamps can be attached in an unclamped state by threading the tube portion through them without any other interconnection.

FIGS. 24A, 24B, 24C, and 24D illustrate schematic diagrams of alternative positions and orientations of locking projection and locking recess that may be used to form further embodiments within the scope of the disclosed subject matter. Each of the pinch clamp embodiments 10, 12, 14, and 16 has a first riser portion 1, a second riser portion 2, a bowl portion 3 and a chin portion 4. The bowl and chin portions 3 and 4 have respective openings (although not shown, but may be as generally as described relative to other embodiments). One or both of the riser portions 1 and 2 may have a pinching projection for squeezing a tube running through the chin and bowl openings (the one or two pinching projections are not shown, but may be as generally as described relative to other embodiments). In embodiment 10, a tapered locking projection 34 can engage with a locking edge or surface 26 on the chin portion 4. This is the general configuration of the disclosed embodiments. In all of embodiments 10, 12, 14, and 16, the end of the strip 5, 6, 7, and 8, having the locking edge or surface 26, 22, 24, and 20, which is opposite the locking projection (although not shown), has a locking recess for guiding the locking projection 34, 30, 32, 28, and a locking opening to receive the locking projection 34, 30, 32, 28. In any of the embodiments 10, 12, 14, or 16, a release tab 48, 44, 46, and 42 may be provided to release the pinch clamp.

In pinch clamp 12, the locking projection 30 faces outwardly and engages a locking edge or surface 22 on the riser 1 that is remote from the chin portion 4 rather than on the chin portion 4. In pinch clamp 14, the locking projection 32 and engages a locking edge or surface 24 on the chin 4, but the locking projection 32 faces inwardly and the locking edge or surface 24 on the chin 4 faces outwardly. In pinch clamp 16, the locking projection 30 faces inwardly and engages a locking edge or surface 20 on the riser 1 that is remote from the chin portion 4 rather than on the chin portion 4.

Figure 25A:
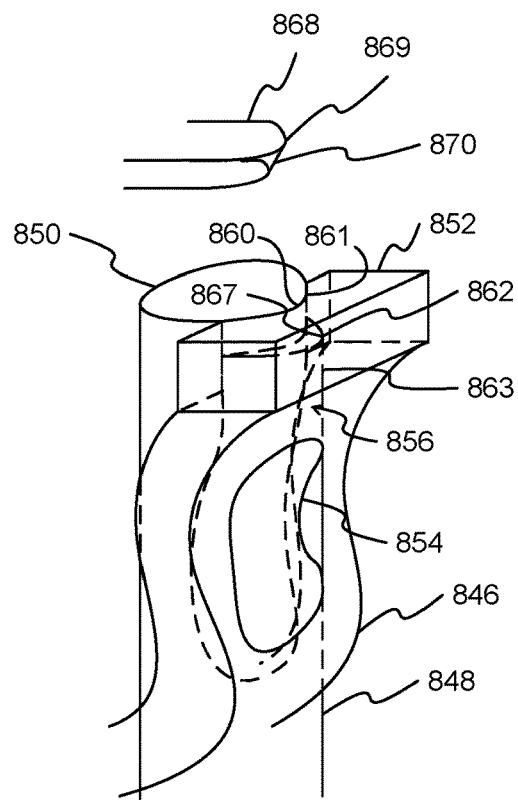
FIGS. 25A and 25B show a feature that may be employed in any of the embodiments in which the locking edge of the locking recess does not define part of the opening in a chin portion of the strip but which feature allows the chin opening and the locking recess edge or surface to be formed using a pin thereby facilitating manufacture.
Figure 25B:
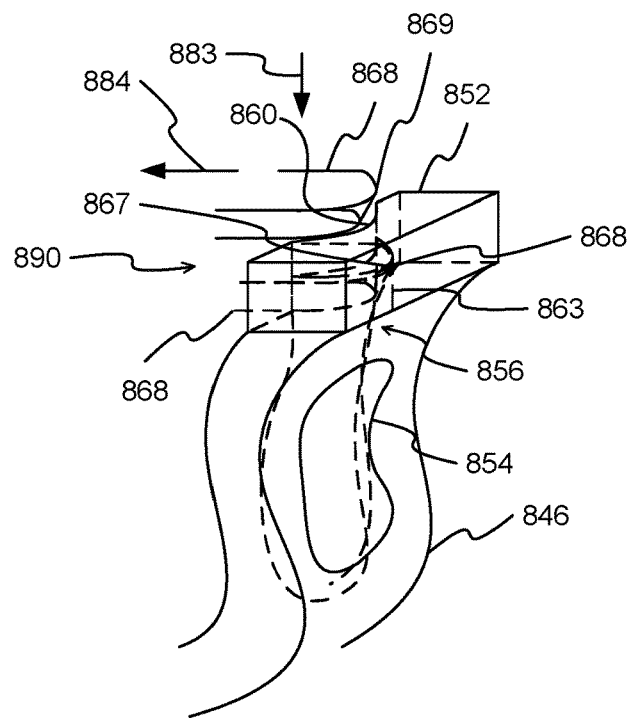

FIGS. 25A and 25B show a feature that may be employed in any of the embodiments in which the locking edge of the locking recess does not define part of the opening in a chin portion of the strip but which feature allows the chin opening and the locking recess edge or surface to be formed using a pin thereby facilitating manufacture. A chin portion 846 of a strip has a chin opening 854 which is created by a pin 848 whose distal end 850 is stepped at a fully distal edge 861 and again, more proximally, at 862. The former step defines a guide recess 861. The latter step 862 of the pin 848 forms a receiving edge or surface 867 that engages a locking edge or surface 869 of a locking projection 868 which may extend from the other end of the strip (not fully shown—only the ends of the strip are shown but may be as described with reference to any of the embodiments). The chin portion 846 may end in a tab portion 852, which may be short as shown or extended as shown in other embodiments. The guide recess 860 guides a tapered surface 870 of the locking projection 868 until it slips into the receiving recess 863 which has an inner end, unlike other embodiments shown where the locking projection slips into the chin opening. Thus, in the present embodiment, the locking recess described with reference to embodiments is divided into a receiving recess 867 and a guide recess 861. Both may be defined by a single pin 848 with the appropriately shaped end as shown.

It will be observed that the embodiments of FIGS. 16A through 19B and 25A and 25B have the feature that a locking recess that provides the locking function and the guiding function can be provided by a feature (a combination of a guide and receiving recess that forms the entire locking recess or a single recess that provides the guide and receiving functions) that is formed by a pin that can be extracted from the pinch clamp (or, equivalently, a pin from which the pinch clamp can be released).

Note that the locking projection 868 moves across the locking recess facing and opening toward a center of pinch clamp such that the locking projection moves in a direction 883 across the facing direction 884 of the receiving recess 867 and that of the guide recess 860 (the combination of the receiving recess 867 and guide recess 860 forming a locking recess 890) when the pinch clamp is manually squeezed. The locking projection only slips into the receiving recess when it engages in which case it moves into the receiving recess rather than across it.

Although the embodiments disclosed show a locking projection stemming from a riser portion opposite a chin portion carrying a locking recess, it is possible to reverse these features between the two riser portions so that the chin portion carries the projection and the opposite riser carries the recess. A release tab on such a reversed structure may still be carried on the chin portion.

Note that in the embodiments disclosed, the chin and bowl openings have no access by means of which the tube may be removed without threading it through the chin or bowl openings. Thus, the chin and bowl openings prevent accidental removal of the pinch clamp from the tube once installed. In alternative embodiments, the chin and/or bowl opening may have a small access that opens to a lateral side, for example, to ensure the clamp cannot be fully or partially removed from the tube, however, such an access may be narrow enough to prevent removal of the tube through such access. Such variations, which prevent accidental removal of the tube or misalignment of the pinch clamp relative to the tube (the latter possibly occurring if the tube escapes one of the bowl and chin openings thereby moving the tube out of alignment with the pinching projections) are within the scope of the embodiments.

Note that any of the embodiments may be revised by using only a single pinching projection and providing a flat or even a recessed surface opposite the single pinching projection. Note that the pinching projection or projections can have a variety of shapes, such as rounded, triangular as illustrated, blade-shaped, etc., the essential requirement being on the effectiveness to at least partially close a tube pinched by it (them).

Although the discussion of the embodiments presumes that edges or surfaces are responsible guiding and locking, for example locking the riser portions of the pinch clamps together. It is understood that a variety of features can perform the interfering engagement function, for example, surface-to-surface abutment, hook and loop fastener, snap fastener devices, and other features. Within the scope of the discussion of the embodiments and the claims, any type of interfering engagement is subsumed under the recitation of engaging edges or surfaces.

According to first embodiments, the disclosed subject matter includes a pinch clamp which is configured as a flexible strip forming a generally U-shaped structure in which ends of riser portions of the U-shape are configured with locking edges or surfaces so as to releasably lock with each other when the riser portions are manually squeezed together. The flexible strip has a bowl portion and a chin portion, the bowl and chin portion have respective chin and bowl openings configured to receive a tube running between them. The chin portion extends from one of the rise portions toward the other of the riser portions. The flexible strip has pinching projecting portions on the riser portions that converge when the riser portions are manually squeezed together, thereby permitting a tube running between the chin and bowl openings to be pinched between the pinching projections. The bowl portion is formed, at least in part, by of a pair of bowl members, defining the bowl opening between them, the bowl members is offset along the direction of a tube axis line joining the chin and bowl openings so that no overhangs exist between the bowl members so that the bowl portion can be formed and released from a two-part mold portion without the use of additional actions or mold elements.

Any of the first embodiments may be modified, where possible, to form additional first embodiments in which the chin portion is defined by another chin members defining the chin opening between them, the chin members are offset along the tube axis line joining the chin and bowl openings so that the chin opening can be formed and released from a two part mold portion without the use of additional actions or mold elements. Any of the first embodiments may be modified, where possible, to form additional first embodiments in which the chin opening has a first locking edge or surface and an upper one of the riser portions which is opposite the chin portion includes a locking projection has a second locking edge or surface, the locking projection is configured to fit in the chin opening to permit the first and second locking edges or surfaces to interferingly engage thereby locking the pinch clamp and pinching a tube between the pinching projections. Any of the first embodiments may be modified, where possible, to form additional first embodiments in which the chin portion has a first anti-cross-clamping surface and the locking projection has a second anti-cross-clamping surface, the first and second anti-cross-clamping surfaces is configured such that the locking projection fits into the chin opening when the first and second anti-cross-clamping surfaces are in contact. Any of the first embodiments may be modified, where possible, to form additional first embodiments in which the chin portion has a first anti-cross-clamping surface and the locking projection has a second anti-cross-clamping surface, the first and second anti-cross-clamping surfaces is configured such that the locking projection fits into the chin opening only when there is no space between the first and second anti-cross-clamping surfaces. Any of the first embodiments may be modified, where possible, to form additional first embodiments in which the chin portion has a first anti-cross-clamping surface and the locking projection has a second anti-cross-clamping surface, the first and second anti-cross-clamping surfaces is configured such that when there is space between the first and second guide edges or surfaces as the pinch clamp is squeezed, there are no edges or surfaces of the riser portions that can engage so as to lock the riser portions together, whereby cross-clamping of a tube between the pinching projections is prevented. Any of the first embodiments may be modified, where possible, to form additional first embodiments in which the locking projection has an asymmetric shape. Any of the first embodiments may be modified, where possible, to form additional first embodiments in which the locking projection has an asymmetric shape with respect to a plane defined by the tube axis line and an imaginary line joining the riser portions. Any of the first embodiments may be modified, where possible, to form additional first embodiments in which the second locking edge or surface is angled away from the first locking edge or surface in a direction remote from the first anti-cross-clamping surface. Any of the first embodiments may be modified, where possible, to form additional first embodiments in which the locking projection has a guide surface that is inclined to push the chin portion away from upper riser portion when the pinch clamp is squeezed. Any of the first embodiments may be modified, where possible, to form additional first embodiments in which the locking projection is configured such that substantially the entire locking projection fits into the chin opening.

According to second embodiments, the disclosed subject matter includes a method of making a pinch clamp, comprising molding a pinch clamp according to any of the foregoing descriptions using a two-part mold.

According to third embodiments, the disclosed subject matter includes a method of making a pinch clamp, comprising releasing a pinch clamp according to any of the foregoing descriptions from a two-part mold, each of the two-part molds has a single recess and no other mold parts defining a portion of the pinch clamp.

According to fourth embodiments, the disclosed subject matter includes pinch clamp which forms a flexible generally U-shaped structure in which the riser portions of the U-shape are shaped so as to engage with each other when the structure's open end is closed by manually pressing the riser portions together. The structure has pinching projections on opposite riser portions that converge when the riser portions are squeezed, thereby permitting a tube running therebetween to be pinched. The structure has no overhangs, thereby permitting the structure to be molded by mold parts that separate from the structure along a single axis.

According to fifth embodiments, the disclosed subject matter includes a method of making a pinch clamp that has a flexible generally U-shaped structure in which the riser portions of the U-shape are shaped so as to engage with each other when the structure's open end is closed by manually pressing the riser portions are urged together. The structure has inwardly projecting portions on opposite riser portions that converge when the riser portions are urged together, thereby permitting a tube running therebetween to be pinched, at least one of the riser portions has a chin portion that extends toward the other of the risers, a bowl portion and the chin portion has openings configured to receive a tube. The fifth embodiment methods include forming the riser portions of the structure using mold parts with facing cavities and projecting at least one pin through at least one of the mold parts, wherein the pin has recesses configured to form sides of the openings, the recesses each has an access opening in a direction that is perpendicular to directions in which the cavities open and separating the mold parts along a first line and removing a molded structure from the pin along a second line that is substantially perpendicular to the first.

According to sixth embodiments, the disclosed subject matter includes releasable pinch clamp which is a flexible, generally U-shaped structure in which first and second riser portions of the U-shape are shaped so as to engage with each other when the structure's open end is closed by manually squeezing the riser portions so that they converge toward each other. A first riser has a tapered locking projection that fits in a locking recess of the second riser before the first and second risers engage with each other as the first and second riser portions are progressively pushed toward each other.

Any of the sixth embodiments may be modified, where possible, to form additional sixth embodiments in which the locking projection is tapered in two dimensions at right angles with respect to each other. Any of the sixth embodiments may be modified, where possible, to form additional sixth embodiments in which the locking recess is rectilinear in shape. Any of the sixth embodiments may be modified, where possible, to form additional sixth embodiments in which the shape of the pinch clamp is such that it can be formed from two opposing mold halves and two pins attached to the same movement mechanism. Any of the sixth embodiments may be modified, where possible, to form additional sixth embodiments in which one of the pins is shaped to define a shape of the recess. Any of the sixth embodiments may be modified, where possible, to form additional sixth embodiments in which the locking recess has a first locking edge or surface and the locking projection has a second locking edge or surface, wherein the first and second locking edges or surfaces are arranged to interferingly engage with each other when the first and second riser portions are sufficiently pushed toward each other. Any of the sixth embodiments may be modified, where possible, to form additional sixth embodiments in which the second riser has a release tab with a grip portion configured for releasing an engagement of the first and second locking edges or surfaces. Any of the sixth embodiments may be modified, where possible, to form additional sixth embodiments in which the grip portion is a single contiguous member that moves as a unit thereby allowing the pinch clamp to be released if any part of the grip portion is manually moved, whereby single-handed operation is facilitated. Any of the sixth embodiments may be modified, where possible, to form additional sixth embodiments in which the second locking edge or surface spans a maximum lateral dimension of the locking projection. Any of the sixth embodiments may be modified, where possible, to form additional sixth embodiments in which the second riser has an opening that is configured to receive a tube. Any of the sixth embodiments may be modified, where possible, to form additional sixth embodiments in which the locking projection fits in the opening. Any of the sixth embodiments may be modified, where possible, to form additional sixth embodiments in which the width of the second locking edge or surface extends across a maximum width of the opening at the first locking edge or surface. Any of the sixth embodiments may be modified, where possible, to form additional sixth embodiments in which the second locking edge or surface cannot interferingly engage the first locking edge or surface without the second locking edge or surface being positioned within the locking recess. Any of the sixth embodiments may be modified, where possible, to form additional sixth embodiments in which the locking recess is configured to guide the locking projection as the first and second risers are manually squeezed together. Any of the sixth embodiments may be modified, where possible, to form additional sixth embodiments in which the first and second risers have facing pinching projections adapted for pinching a flexible tube positioned therebetween when the first and second risers are manually squeezed together. Any of the sixth embodiments may be modified, where possible, to form additional sixth embodiments in which the generally U-shaped structure retains a shape such that the first and second risers are in a configuration to allow them to be manually squeezed together with a pinching action without being held by an interconnection between said first and second riser portions.

According to seventh embodiments, the disclosed subject matter includes a pinch clamp for selectively pinching a tube closed and opening the tube by releasing the pinch clamp. The pinch clamp is generally a strip defining a generally U-shaped structure that has a bowl portion, a first riser portion with a chin portion extending from the riser portion, and a second riser portion. The bowl and chin portions have bowl and chin openings configured to receive a tube therethrough. The bowl and chin portions surround the bowl and chin openings so as to prevent a predefined tube from exiting either the bowl or chin opening without threading the tube out of the respective bowl and chin openings. One of the first riser portion and the chin portion has a locking recess with a first locking edge or surface and the other of the first riser portion and the chin portion has a locking projection with a second locking edge or surface. The one of the first riser portion and the chin portion has a locking opening adjacent the recess configured to receive the locking projection therein. The first and second locking edges or surfaces are configured to engage the first locking edge or surface when the locking projection inserts in the locking opening. The locking projection is shaped so as to be progressively guided to a lateral position in which the locking projection can enter the locking opening as the first and second riser portions are squeezed together. The pinch clamp is configured such that there are no edges or surfaces on either of the first riser portion and the chin that can interferingly engage with each other in order to lock the first and second riser portions together in a potentially cross-clamping state without the locking projection is inserted in the locking opening.

Any of the seventh embodiments may be modified, where possible, to form additional seventh embodiments in which the one of the one of the first riser portion and the chin portion is the chin portion. Any of the seventh embodiments may be modified, where possible, to form additional seventh embodiments in which the locking projection has a pyramid or cone shape. Any of the seventh embodiments may be modified, where possible, to form additional seventh embodiments in which the pinch clamp is configured such that it can be molded using a two-part mold and no more than two pins, wherein the two pins can be used to form the chin and bowl openings. Any of the seventh embodiments may be modified, where possible, to form additional seventh embodiments in which the locking projection has a distal end which inserts in the locking opening and the locking surface or edge extends across the entirety of the locking projection distal end so that the locking edge of surface of the locking edge is required to fit into the locking opening in order to lock the riser portions together to clamp a tube threaded through the chin and bowl openings. Any of the seventh embodiments may be modified, where possible, to form additional seventh embodiments in which one of the first riser portion and the chin portion has a release tab arranged such that when manually pressed, releases engagement between the locking edges or surfaces. Any of the seventh embodiments may be modified, where possible, to form additional seventh embodiments in which the locking projection is tapered in two dimensions at right angles with respect to each other. Any of the seventh embodiments may be modified, where possible, to form additional seventh embodiments in which the locking recess is rectilinear in shape. Any of the seventh embodiments may be modified, where possible, to form additional seventh embodiments in which the release tab is a single contiguous member that moves as a unit thereby allowing the pinch clamp to be released if any part of the release tab is manually moved, whereby single-handed operation is facilitated. Any of the seventh embodiments may be modified, where possible, to form additional seventh embodiments in which the locking recess is configured to guide the locking projection as the first and second risers are manually squeezed together. Any of the seventh embodiments may be modified, where possible, to form additional seventh embodiments in which the first and second risers have facing, pinching projections adapted for pinching a flexible tube positioned therebetween when the first and second risers are manually squeezed together. Any of the seventh embodiments may be modified, where possible, to form additional seventh embodiments in which the first and second risers have facing, pinching projections adapted for pinching a flexible tube threaded through the chin and bowl openings when the first and second risers are manually squeezed together. Any of the seventh embodiments may be modified, where possible, to form additional seventh embodiments in which the generally U-shaped structure retains its shape such that the first and second risers are in a configuration to allow them to be manually squeezed together with a pinching action without being held by an interconnection between said first and second riser portions.

The disclosed subject matter also includes haptic pinch clamps that generate a specific pattern of haptic feedback. The embodiments may be variants of any of the embodiments described (including the first through eighth embodiments and the described variations thereof) that have a chin opening, a locking projection, and locking edges or surfaces. In these haptic pinch clamps, the locking edges or surfaces are further configured such that as the pinch clamp is manually squeezed, the locking projection first enters the chin opening generating a haptic feedback resulting from the slipping of the locking projection into the chin opening and as a result of further squeezing, the chin locking edge or surface rests temporarily on an initial landing surface and upon release of the squeezing pressure of the pinch clamp, the chin locking edge rides the initial landing surface to a step over which the chin locking edge falls finally to resting on the locking projection locking surface or edge, thereby causing a second haptic feedback. The effect of these is that the user feels a click sensation upon pinching and a second click sensation during release.

According to eighth embodiments, the disclosed subject matter includes a pinch clamp with a main member with opposing ends that can be squeezed together manually and configured to be attached to a tube and further configured to pinch an attached tube when the main member is manually squeezed to a pinching configuration. The opposing ends have locking members that engage when the opposing ends are manually squeezed together resulting in maintaining the pinching configuration of the main member. The locking members are configured to generate a first haptic feedback when the pinching configuration is reached and a second haptic feedback when the pinching force is released.

Any of the eighth embodiments may be modified, where possible, to form additional eighth embodiments in which the locking features include a stepped member of one locking member having a sloping initial landing surface that leads to a step which then leads to a final landing surface, an edge or surface of the other locking member engaging the sloping initial landing surface when the main member is manually squeezed beyond the pinching configuration and slipping off the step and resting on the final landing surface to maintain the pinching configuration of the main member. Any of the eighth embodiments may be modified, where possible, to form additional eighth embodiments in which the one locking member includes a projecting portion that fits in an opening defined in part by the other locking member. Any of the eighth embodiments may be modified, where possible, to form additional eighth embodiments in which the opening is adapted for receiving a tube. Any of the eighth embodiments may be modified, where possible, to form additional eighth embodiments that include an attached tube. Any of the eighth embodiments may be modified, where possible, to form additional eighth embodiments in which the attached tube is a portion of fluid circuit and enclosed in a sterile container. Any of the eighth embodiments may be modified, where possible, to form additional eighth embodiments in which the main member is a single plastic element with one or two inwardly projecting pinching elements arranged to pinch a tube. Any of the eighth embodiments may be modified, where possible, to form additional eighth embodiments in which the locking members include, between them, a release member that provides a grip surface and is configured to release the pinching configuration of the main member upon actuation thereof. Any of the eighth embodiments may be modified, where possible, to form additional eighth embodiments in which one of the locking members is configured to prevent lateral displacement of the other of the locking members during initial manual squeezing so as to guide the one of the locking members with respect to the other of the locking members, thereby to prevent cross-clamping.

The pinch clamp of any of the disclosed pinch clamp embodiments may be modified such that the pinch clamp is a single component with only integrally connected parts or features. The pinch clamp of any of the disclosed pinch clamp embodiments may be modified such that the pinch clamp is configured for use in pinching closed medical tubing. The pinch clamp of any of the disclosed pinch clamp embodiments may be modified such that the pinch clamp is of plastic. The pinch clamp of any of the disclosed pinch clamp embodiments may be modified such that the pinch clamp has a maximum dimension that is less than 3 cm.

According to ninth embodiments, the disclosed subject matter includes a pinch clamp with a main member with riser portions that are arranged such that an opposing pinching force flexes a middle portion of the main member and thereby permits first and second riser portions to be squeezed together. The ends of the first and second riser portions have respective locking portions that lock together so that when the first and second riser portions are squeezed together a certain amount, the first and second riser portions are locked a fixed distance apart. The first and second riser portions have between them at least one pinching projection configured to pinch a tube. The first riser portion is shaped, at an end thereof, to fit into a slot defined in the second riser portion. The second riser portion has an opening into which the first riser portion end fits, the opening is adapted for fully surrounding a tube and guiding the tube into alignment with the at least one pinching projection. The slot is configured to maintain the first riser portion end in a predefined range of lateral positions as the riser portions are squeezed together until the first riser portion end aligns with the opening whereupon, as a result of the configuration of the main member, the first riser portion end is urged into the opening thereby locking the first and second riser portions into a squeezed position enabling a tube to be pinched by said at least one pinching projection. A surface or edge defines the opening constituting a locking surface or edge that by virtue of its engagement with a major surface of the first riser end, provides the means by which the first and second riser portions are maintained in the squeezed position.

Any of the ninth embodiments may be modified, where possible, to form additional ninth embodiments in which the slot defined in the second riser portion is a recess with an inner end. Any of the ninth embodiments may be modified, where possible, to form additional ninth embodiments in which the slot defined in the second riser portion leads continuously to the opening. Any of the ninth embodiments may be modified, where possible, to form additional ninth embodiments in which the slot defined in the second riser portion leads continuously to the opening such that the opening and the slot can be defined by a cylindrical surface.

According to tenth embodiments, the disclosed subject matter includes a pinch clamp having a main member with opposing ends that can be squeezed together manually and configured to be attached to a tube and further configured to pinch an attached tube when the main member is manually squeezed to a pinching configuration. The opposing ends have locking members that engage when the opposing ends are manually squeezed together resulting in maintaining the pinching configuration of the main member. The locking members are configured to generate a first haptic feedback when the pinching configuration is reached and a second haptic feedback when a pinching force is released.

Any of the tenth embodiments may be modified, where possible, to form additional tenth embodiments in which the locking features include a stepped member of one locking member having a sloping initial landing surface that leads to a step which then leads to a final landing surface, an edge or surface of the other locking member engaging the sloping initial landing surface when the main member is manually squeezed beyond the pinching configuration and slipping off the step and resting on the final landing surface to maintain the pinching configuration of the main member. Any of the tenth embodiments may be modified, where possible, to form additional tenth embodiments in which the one locking member includes a projecting portion that fits in an opening defined in part by the other locking member. Any of the tenth embodiments may be modified, where possible, to form additional tenth embodiments in which the opening is adapted for receiving a tube. Any of the tenth embodiments may be modified, where possible, to form additional tenth embodiments which have an attached tube. Any of the tenth embodiments may be modified, where possible, to form additional tenth embodiments in which the attached tube is a portion of fluid circuit and enclosed in a sterile container. Any of the tenth embodiments may be modified, where possible, to form additional tenth embodiments in which the main member is a single plastic element with one or two inwardly projecting pinching elements arranged to pinch a tube. Any of the tenth embodiments may be modified, where possible, to form additional tenth embodiments in which the locking members include, between them, a release member that provides a grip surface and is configured to release the pinching configuration of the main member upon actuation thereof. Any of the tenth embodiments may be modified, where possible, to form additional tenth embodiments in which one of the locking members are configured to prevent lateral displacement of the other of the locking members during initial manual squeezing so as to guide the one of the locking members with respect to the other of the locking members, thereby to prevent cross-clamping.

According to eleventh embodiments, the disclosed subject matter includes a pinch clamp with a flexible member that has riser portions with respective locking portions that have locking edges or surfaces which interferingly engage to lock the riser portions together when the pinch clamp is manually squeezed, one riser portion locking portion includes a locking projection that fits into a receiving recess or opening of the locking portion of the other riser portion, the other riser portion also has a projection-guide-lock portion with a receiving recess or opening configured to receive said locking projection The riser portion extends away from a bowl portion generally in a first direction along a direction of longitudinal axes of said riser portions. The flexible member has tube-aligning openings for receiving a tube and one or more pinching projections positioned to pinch the tube when the riser portions of the flexible member are squeezed together. The projection-guide-lock portion is configured such that the receiving recess is adjacent to, or coincides with, a guide recess, where the guide recess has an inner end. The locking recess is shaped such that there are no overhanging portions of a surface defining the locking recess from a view direction along a third direction that forms an angle with respect to the first direction and a second direction, such that the locking recess can be molded by a removable mold portion, the second direction extending parallel to a line between the ends of the risers. The locking recess faces and opens toward a center of the pinch clamp such that the locking projection moves in a direction across the facing direction of the recess when the pinch clamp is manually squeezed.

Any of the eleventh embodiments may be modified, where possible, to form additional eleventh embodiments in which the locking recess has a separate guide recess. Any of the eleventh embodiments may be modified, where possible, to form additional eleventh embodiments in which the guide recess access continues across the receiving recess access so as to form a single enlarged access of the combination of the guide recess access and receiving recess access. Any of the eleventh embodiments may be modified, where possible, to form additional eleventh embodiments in which the locking projection is tapered so that it is progressively aligned with the receiving recess as the pinch clamp is manually squeezed. Any of the eleventh embodiments may be modified, where possible, to form additional eleventh embodiments in which there are no edges or surfaces on either of the riser portions that can interferingly engage with each other in order to lock the riser portions together other than by the locking projection is received within the receiving recess or opening.

Any of the eleventh embodiments may be modified, where possible, to form additional eleventh embodiments in which there are no edges or surfaces on either of the riser portions that can interferingly engage with each other in order to lock the riser portions together in a configuration in which a tube received in said tube-aligning openings is cross-clamped by said one or more pinching projections. Any of the eleventh embodiments may be modified, where possible, to form additional eleventh embodiments in which the receiving recess or opening is one of said tube-aligning openings. Any of the eleventh embodiments may be modified, where possible, to form additional eleventh embodiments in which the guide recess inner end is defined by a manually engageable release tab extending from the other depending portion. Any of the eleventh embodiments may be modified, where possible, to form additional eleventh embodiments in which the locking projection is configured such that substantially the entire width of the locking projection fits into the receiving recess. Any of the eleventh embodiments may be modified, where possible, to form additional eleventh embodiments in which the locking portions are configured such that when the pinch clamp is pinched and then released, respective first and second haptic feedback impulses are generated that give the feeling of first and second palpable clicks thereby confirming locking engagement.

Any of the eleventh embodiments may be modified, where possible, to form additional eleventh embodiments in which the haptic feedback is generated by the locking projection first entering the receiving recess, generating a first haptic feedback resulting from the slipping of the locking projection into the receiving recess and as a result of further squeezing, an edge of one of the locking portions landing initially on a landing surface and upon release of the squeezing pressure of the pinch clamp, the edge rides the landing surface to a step over which the edge falls thereby causing a second haptic feedback. Any of the eleventh embodiments may be modified, where possible, to form additional eleventh embodiments in which the pinch clamp is connected to a fluid circuit adapted for use in a medical treatment device. Any of the eleventh embodiments may be modified, where possible, to form additional eleventh embodiments in which the tube aligning openings are fully closed such that a tuber extending through them is fully surrounded leaving no access to permit the tube to be placed in the tube aligning openings without threading it therethrough. Any of the eleventh embodiments may be modified, where possible, to form additional eleventh embodiments in which the locking edges or surfaces are configured such that it can be manually released by moving a single grip surface of said pinch clamp thereby to unpinch a tube pinched by said pinch clamp.

The double haptic feedback "click" may be provided by various means and incorporated in any of the disclosed embodiments. Generally the feedback may produce a first click when squeezed and then another click upon partial or full release.

In many of the embodiments, a single locking recess is described for guiding the locking projection and providing a locking edge or surface below it to interferingly engage the locking projection. As described with reference to the embodiments of FIGS. 25A and 25B, the function can be provided respectively by guiding and receiving recesses. Variation of all the disclosed embodiments may include such a combination of guiding and receiving recesses instead of a single locking recess. This discussion is intended to apply to the embodiments defined by the claims as well.

The disclosed embodiments include an article of manufacture that includes the pinch clamp of any of the embodiments sealed in a sterile envelope. Any of the described pinch clamps may be attached to a tube to form an article of manufacture such as a tubing set. The latter may be packaged in a sterile pouch or envelope.

Any of the disclosed pinch clamps may be for use in or connected to a fluid circuit adapted for use in a medical treatment device.

The pinch clamp of any of the embodiments may have the bowl and chin openings fully closed such that the bowl portion fully surrounds the bowl opening and the chin portion fully surrounds the chin opening leaving no access and whereby a tube must be threaded therethrough.

In all of the embodiments with a locking recess, the recess has an inner end such that the structure behind it, for example a respective release tab of the embodiments with a release tab, is a contiguous member which defines a closed opening therebelow. (Note an inner end is a characteristic of all recesses, essentially defining the end of the recess opposite the access.) The opening receives locking projection in the embodiments, but it is also possible that the locking projection may be received in a recess rather than an opening, for example, a chin opening that receives a tube. The illustrated embodiments have the feature of the locking recess being continuous with the opening that admits the tube because, as described with reference to FIG. 18B, it is possible to form this recess and the opening easily with a pin. Note that the pin 730 can be a cylindrical surface with stepped cut at its end which is inexpensive to machine precisely. Alternatively it can be a conical section or a cylinder with a taper toward the stepped end.

It is, thus, apparent that there is provided, in accordance with the present disclosure, devices for clamping tubing and methods and devices for making and methods for using the same. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicant intends to embrace all such alternatives, modifications, equivalents, and variations that are within the spirit and scope of the present invention.

The invention claimed is:

1. A method of making a pinch clamp, the pinch clamp having a flexible generally U-shaped structure in which riser portions of the U-shape are shaped so as to engage with each other when an open end of the structure is closed by manually pressing the riser portions so as to urge them together, the structure having inwardly projecting portions on opposite riser portions that converge when the riser portions are urged together, thereby permitting a tube running therebetween to be pinched, at least one of the riser portions having a chin portion that extends toward the other of the risers, the structure further comprising a bowl portion, and the chin portion and the bowl portion having openings configured to receive a tube, the method comprising:
    forming the riser portions of the structure using mold parts with facing cavities and projecting at least one pin through at least one of the mold parts, wherein the pin has recesses configured to form sides of the openings, the recesses each having an access opening in a direction that is perpendicular to directions in which the cavities open;
    separating the mold parts along a first line and removing a molded structure from the pin along a second line that is substantially perpendicular to the first.

2. A pinch clamp, comprising:
    a flexible strip forming a generally U-shaped structure in which ends of riser portions of the U-shape are configured with locking edges or surfaces so as to releasably lock with each other when the riser portions are manually squeezed together;
    the flexible strip having a bowl portion and a chin portion having respective bowl and chin openings configured to receive a tube running between them;
    the chin portion extending from one of the riser portions toward the other of the riser portions;
    the flexible strip having pinching projecting portions on the riser portions that converge when the riser portions are manually squeezed together, thereby permitting a tube running between the chin and bowl openings to be pinched between the pinching projections;
    the bowl portion being formed, at least in part, by of a pair of bowl members, defining the bowl opening between them, the bowl members being offset along a direction of a tube axis line joining the chin and bowl openings so that no overhangs exist between the bowl members so that the bowl portion can be formed and released from a two part mold portion without use of additional actions or mold elements.

3. The pinch clamp of claim 2, wherein the chin portion is defined by other chin members defining the chin opening between them, the chin members being offset along the tube axis line joining the chin and bowl openings so that the chin opening can be formed and released from a two part mold portion without the use of additional actions or mold elements.

4. The pinch clamp of claim 3, wherein the chin opening has a first locking edge or surface and an upper one of the riser portions which is opposite the chin portion includes a locking projection having a second locking edge or surface, the locking projection being configured to fit in the chin opening to permit the first and second locking edges or surfaces to interferingly engage thereby locking the pinch clamp and pinching a tube between the pinching projections.

5. The pinch clamp of claim 4, wherein the locking projection is configured such that substantially an entirety of the locking projection fits into the chin opening.

6. The pinch clamp of claim 2, wherein the chin opening has a first locking edge or surface and an upper one of the riser portions which is opposite the chin portion includes a locking projection having a second locking edge or surface, the locking projection being configured to fit in the chin opening to permit the first and second locking edges or surfaces to interferingly engage thereby locking the pinch clamp and pinching a tube between the pinching projections.

7. The pinch clamp of claim 6, wherein the chin portion has a first anti-cross-clamping surface and the locking projection has a second anti-cross-clamping surface, the first and second anti-cross-clamping surfaces being configured such that the locking projection fits into the chin opening when the first and second anti-cross-clamping surfaces are in contact.

8. The pinch clamp of claim 7, wherein the locking projection has an asymmetric shape.

9. The pinch clamp of claim 7, wherein the locking projection has an asymmetric shape with respect to a plane defined by the tube axis line and an imaginary line joining the riser portions.

10. The pinch clamp of claim 9, wherein the second locking edge or surface is angled away from the first locking edge or surface in a direction remote from the first anti-cross-clamping surface.

11. The pinch clamp of claim 7, wherein the locking projection has a guide surface that is inclined to push the chin portion away from upper riser portion when the pinch clamp is squeezed.

12. The pinch clamp of claim 6, wherein the chin portion has a first anti-cross-clamping surface and the locking projection has a second anti-cross-clamping surface, the first and second anti-cross-clamping surfaces being configured such that the locking projection fits into the chin opening only when there is no space between the first and second anti-cross-clamping surfaces.

13. The pinch clamp of claim 6, wherein the locking projection has an asymmetric shape.

14. The pinch clamp of claim 12, wherein the locking projection has an asymmetric shape with respect to a plane defined by the tube axis line and an imaginary line joining the riser portions.

15. The pinch clamp of claim 14, wherein the second locking edge or surface is angled away from the first locking edge or surface in a direction remote from the first anti-cross-clamping surface.

16. The pinch clamp of claim 6, wherein the chin portion has a first anti-cross-clamping surface and the locking projection has a second anti-cross-clamping surface, the first and second anti-cross-clamping surfaces being configured such that when there is space between first and second guide edges or surfaces as the pinch clamp is squeezed, there are no edges or surfaces of the riser portions that can engage so as to lock the riser portions together, whereby cross-clamping of a tube between the pinching projections is prevented.

17. The pinch clamp of claim 16, wherein the locking projection has an asymmetric shape.

18. The pinch clamp of claim 16, wherein the locking projection has an asymmetric shape with respect to a plane defined by the tube axis line and an imaginary line joining the riser portions.

19. The pinch clamp of claim 18, wherein the second locking edge or surface is angled away from the first locking edge or surface in a direction remote from the first anti-cross-clamping surface.

20. The pinch clamp of claim 6, wherein the locking projection has a guide surface that is inclined to push the chin portion away from upper riser portion when the pinch clamp is squeezed.

* * * * *